United States Patent
Maeshima

(10) Patent No.: US 8,906,304 B2
(45) Date of Patent: Dec. 9, 2014

(54) SAMPLE PROCESSING DEVICE, SAMPLE TREATMENT METHOD, AND REACTION CONTAINER USED IN THESE DEVICE AND METHOD

(75) Inventor: Muneo Maeshima, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/122,325

(22) PCT Filed: May 21, 2012

(86) PCT No.: PCT/JP2012/062891
§ 371 (c)(1),
(2), (4) Date: Nov. 26, 2013

(87) PCT Pub. No.: WO2012/165187
PCT Pub. Date: Dec. 6, 2012

(65) Prior Publication Data
US 2014/0087370 A1    Mar. 27, 2014

(30) Foreign Application Priority Data
May 30, 2011  (JP) .................................. 2011-119955

(51) Int. Cl.
*G01N 21/00*    (2006.01)
(Continued)

(52) U.S. Cl.
CPC ........ *C12N 15/1013* (2013.01); *G01N 35/1067* (2013.01); *G01N 2035/103* (2013.01);
(Continued)

(58) Field of Classification Search
None
See application file for complete search history.

(56) References Cited

U.S. PATENT DOCUMENTS 6,764,859 B1      7/2004  Kreuwel et al.
2004/0157224 A1*  8/2004  Roh et al. .......................... 435/6
(Continued)

FOREIGN PATENT DOCUMENTS

JP    2003-504195 A    2/2003
JP    2004-229657 A    8/2004
(Continued)

OTHER PUBLICATIONS

Boom, R., Sol, C. J. A. Salimans, M. M. M., Jansen, C. L, Wertheimvan Dillien, P. M. E., and van der Noordaa, J., J. Clin. Microbiol., 28, 495-503 (1990).

(Continued)

*Primary Examiner* — Jill Warden
*Assistant Examiner* — Julie Tavares
(74) *Attorney, Agent, or Firm* — Mattingly & Malur, PC

(57) ABSTRACT

Reaction containers (110) each comprising a plurality of treatment parts (wells) (501-506) are placed side by side in a reaction container set so as to be movable independently of each other in the direction of arrangement of the treatment parts (wells). A plurality of stems (401) correspond to the respective reaction containers (110) and are disposed above the reaction containers to be vertically movable and disposed in the direction crossing the direction of movement of the reaction containers. Control is performed so that when the reaction containers (110) and a stem mechanism (111) are operated together and one of the treatment parts (501-506) of each of the reaction containers (110) comes immediately below the stem mechanism (111) in accordance with a treatment procedure, a stem (401) corresponding thereto, a magnetic chip (402) attached thereto, or the cover (405) thereof can go into and out of the treatment part.

12 Claims, 20 Drawing Sheets

(51) Int. Cl.
*G01N 31/00* (2006.01)
*G01N 33/00* (2006.01)
*G01N 35/00* (2006.01)
*G01N 35/02* (2006.01)
*C12N 15/10* (2006.01)
*G01N 35/10* (2006.01)

(52) U.S. Cl.
CPC ......... *G01N 35/0099* (2013.01); *G01N 35/109* (2013.01); *G01N 35/026* (2013.01); *G01N 35/10* (2013.01); *G01N 35/02* (2013.01)
USPC .................. 422/65; 422/62; 422/67; 422/501

(56) References Cited

U.S. PATENT DOCUMENTS

| | | |
|---|---|---|
| 2006/0144169 A1 | 7/2006 | Porat et al. |
| 2006/0269385 A1 | 11/2006 | Zobel et al. |
| 2007/0077174 A1* | 4/2007 | Sugiyama et al. ............. 422/65 |
| 2008/0014610 A1 | 1/2008 | Kamata et al. |
| 2008/0171337 A1 | 7/2008 | Miyazaki et al. |
| 2009/0176308 A1 | 7/2009 | Griebel et al. |
| 2009/0181359 A1 | 7/2009 | Lou et al. |
| 2011/0300565 A1 | 12/2011 | Furusato et al. |
| 2012/0309104 A1 | 12/2012 | Uematsu et al. |

FOREIGN PATENT DOCUMENTS

| | | |
|---|---|---|
| JP | 2004-337137 A | 12/2004 |
| JP | 2005-037179 A | 2/2005 |
| JP | 2006-329986 A | 12/2006 |
| JP | 2007-279006 A | 10/2007 |
| JP | 2008-167722 A | 7/2008 |
| JP | 2011-501194 A | 1/2011 |
| JP | 2011-127965 A | 6/2011 |
| JP | 2012-247330 A | 12/2012 |
| JP | 5292267 B2 | 6/2013 |
| JP | 2013-145251 A | 7/2013 |
| WO | 2005-118803 A1 | 12/2005 |

OTHER PUBLICATIONS

Notice of filings of publications from the Japanese Patent Office for JP2011-119955 dated Dec. 3, 2013.

* cited by examiner

SAMPLE PROCESSING DEVICE, SAMPLE TREATMENT METHOD, AND REACTION CONTAINER USED IN THESE DEVICE AND METHOD

TECHNICAL FIELD

The present invention relates to a sample processing device and a sample processing method for implementing various types of processing associated with extraction, separation, purification, and other forms of processing of biological molecules, such as nucleic acids and proteins, originally in a sample containing cells, bacteria, viruses, and the like. Also, the present invention relates to a reaction container used in such a sample processing device and a sample processing method.

BACKGROUND ART

Extraction, separation, and purification of biological molecules, such as nucleic acids and proteins, from biological samples, such as blood, blood plasma, or tissue slice samples, are fundamental, important procedures in order to obtain test substances in research on life phenomena in biological or medical field. The above procedures are used not only in the research on the life phenomena but are also used to obtain test substances in industries involved with plant variety improvement for agricultural crops, food inspection, and the like.

Regarding nucleic acid testing, in particular, polymerase chain reaction (PCR) techniques capable of DNA or RNA amplification have become common. In addition, various nucleic acid amplification techniques, such as the nucleic acid sequence-based amplification (NASBA) technique, the strand displacement amplification (SDA) technique, the self-sustained sequence replication (3SR) technique, the transcription-mediated amplification (TMA) technique, the Qβ replicase amplification technique, and the loop-mediated isothermal amplification (LAMP) technique, have been developed. Accordingly, the nucleic acid testing application range is expanding, and it is considered that demands for techniques of quicker and simpler extraction, separation and purification of nucleic acids from biological samples will keep increasing.

Phenol/chlorophorm extraction has been known as a technique for extracting, separating, and purifying a nucleic acid such as DNA or RNA from a biological sample. This technique, however, imposed serious burdens on those performing it due to the use of organic solvent or complicated procedures. In order to overcome the drawbacks described above, as a technique of extracting, separating, and purifying nucleic acids from a biological sample, a method utilizing the ability of nucleic acids to bind to silica or glass fibers in the presence of a chaotropic agent (e.g., Non Patent Literature 1) was proposed, and an automatic apparatus for implementing nucleic acid extraction was developed (e.g., Patent Literature 1 and 2).

The process of nucleic acid extraction, separation, and purification that is generally carried out with the use of an automatic apparatus is as described in (1) to (6) below.

(1) Cells contained in a biological sample are fractured with a solution containing a chaotropic agent or surfactant to elute nucleic acids in the solution. (2) Silica-coated magnetic beads (i.e., magnetic silica particles) are added to the solution and mixed therein to allow nucleic acids to absorb onto the particle surface. (3) A magnet is brought into approximate contact therewith from the outside of a reaction container, and a solution containing unnecessary substances, such as proteins, is removed with the used of a pump or other means while magnetic beads remain captured in the reaction container. (4) A wash solution is added to the reaction container, and unnecessary substances are allowed to migrate into the solution. (5) A magnet is brought into approximate contact therewith from the outside of a reaction container again, and a solution containing unnecessary substances is removed while magnetic beads remain captured in the reaction container. (6) Magnetic beads are introduced into sterilized water or low-salt buffer after the wash solution has been removed in order to elute nucleic acids from the magnetic bead surface.

CITATION LIST

Patent Literature

PTL 1: Japanese Patent Application Laid-Open No. 2003-504195

PTL 2: Japanese Patent Application Laid-Open No. 2004-337137

Non Patent Literature

NPTL 1: Boom, R., Sol, C. J. A. Salimans, M. M. M., Jansen, C. L., Wertheimvan Dillien, P. M. E., and van der Noordaa, J., J. Clin. Microbiol., 28, 495-503 (1990).

SUMMARY OF INVENTION

Technical Problem

As a shift of markets from clinical researches to clinical inspections, there arise increasing needs of successively processing a randomly provided specimen as appropriate and more quickly feeding back test results on diagnosis.

A device described in PTL 1, upon processing of a plurality of samples, performs so-called batch processing in which a plurality of samples are processed at the same time, and does not perform successive processing, as appropriate, on randomly provided specimen. The automation device described in PTL 2, upon processing of a plurality of samples, "installs a plurality of sets of extraction devices in the device main body", requiring a vertical and horizontal movement mechanism for a plurality of arms and a large number of driving parts such as a movement mechanism for a plurality of arm positions. Moreover, it is described in PTL 2 that a plurality of sample containers can be loaded at the same time, but can be processed at the same time, and it is batch processing of allowing driving parts of a plurality of extraction devices to perform the same operation in cooperation with each other, and thus it also cannot successively process, as appropriate, randomly provided specimens.

It is an object of the present invention to provide a sample processing device and a sample processing method capable of performing batch processing on a biological sample (for example, specimen) in a device performing a series of processing by causing the biological sample to react with a reagent and also capable of performing successive processing through random introduction, and a reaction container using them.

Solution to Problem

To address the object described above, first, a sample processing device as described below is provided.
(Sample Processing Device 1)

Specifically, a sample processing device including a reaction container where a series of processing is performed by causing reaction of a biological sample with a reagent, the reaction container being provided with a plurality of processing parts arranged in a manner such that the series of processing is performed, includes:

a reaction container set part allowing a plurality of the reaction containers to be arranged in parallel thereon;

a reaction container movement mechanism moving the reaction containers set on the reaction container set part in an arrangement direction of the processing parts independently on an individual reaction container basis;

a stem mechanism in which a plurality of stems used for the series of processing in cooperation with the reaction containers are arranged above the reaction container set part in correspondence with the respective reaction containers in a manner such as to be movable vertically, and the stems form a row in a direction crossing a moving direction of the reaction containers and are arranged at a pitch in accordance with a pitch between the processing parts of the reaction containers arranged in parallel on the reaction container set part;

a stem vertical movement mechanism vertically moving the stem mechanism; and a control part interlocking the reaction container movement mechanism and the stem vertical movement mechanism for the series of processing, and performing control of entrance and leaving of the corresponding stem or a tool fitted thereto into and from the processing part when the corresponding processing part of each reaction container comes immediately below the stem mechanism in accordance with processing procedures.

Moreover, to address the object described above, the sample processing device according to the present invention optionally includes the following embodiments.

(Auxiliary Embodiments)

(1) The reaction container is for extracting at least a biological molecule from the biological sample by use of a reagent and a magnetic bead, and includes, as the processing parts:

a reaction part to which the biological sample, the regent for the biological molecule extraction, and the magnetic bead for biological molecule absorption;

a magnetic chip housing part housing, for the purpose of attaching and detaching the stem, a magnetic chip used for collecting the magnetic bead absorbed to the biological molecule;

a cover housing part housing a cover of the magnetic chip for the purpose of attaching and detaching the stem;

a washing part storing a wash solution for washing the magnetic bead absorbing the biological molecule; and an eluting part receiving the washed magnetic bead and eluting the biological molecule from a surface of the magnetic bead.

(2) The stem mechanism is an integral stem mechanism in which the plurality of stems are supported integrally in a manner such as to be vertically movable, the stem vertical movement mechanism has a mechanism of causing the integral stem mechanism to make a cyclic, vertical motion by one driving source through a control signal from the control part, and the reaction container movement mechanism is subjected to movement control by the control part in accordance with the cyclic, vertical motion of the stem vertical movement mechanism so that the plurality of processing parts come immediately below the stem vertical movement mechanism in accordance with the processing procedures.

(3) The reaction container movement mechanism linearly moves the reaction containers set on the reaction container set part, or moves the reaction containers set on the reaction container set part in a rotation direction with one axis as a center.

(4) The magnetic chip and the cover each have an opening at a base end thereof opposite to a tip thereof, an inner diameter of the opening is larger for the cover than for the magnetic chip, and a fringe region is provided at a circumference edge of each opening, in the stem, different outer diameter parts for attaching and detaching the magnetic chip and the cover through the respective openings are provided from a stem tip side to a stem middle region, and the reaction container is provided with an attachment and detachment mechanism of engaging and separating the magnetic chip or the cover by moving the magnetic chip or the cover in a decentered manner via the reaction container with respect to the processing part when the magnetic chip or the cover is inserted into the processing part.

(5) The attachment and detachment mechanism is composed of an upper retainer plate and a lower retainer plate being provided above the opening of the processing part oppositely thereto, the retainer plates being provided with notch regions with different curvatures receiving the movement in the decentered manner in accordance with outer diameters of the magnetic chip and the cover, and the notch regions are arranged in a moving direction of the reaction containers and an opening of each of the notch regions is also directed in the moving direction of the reaction containers.

(Sample Processing Device 2)

Further, suggested is a sample processing device 2 including, in addition to components of the sample processing device 1 described above, the reaction container, where a series of processing related to at least extraction of a biological molecule from a biological sample by using a reagent and a magnetic bead is performed, including, as the processing parts, at least:

a reaction part to which the biological sample, the reagent for the biological molecule extraction, and the magnetic bead for biological molecule absorption are supplied;

a magnetic chip housing part housing a magnetic chip used for collecting the magnetic bead absorbing the biological molecule, for the purpose of attaching and detaching the magnetic chip to and from the stem; and a cover housing part housing a cover of the magnetic chip for the purpose of attaching and detaching the cover to and from the stem, (Sample Processing Method)

By using the sample processing device 2, the following sample processing method is suggested.

In a sample processing method performing a series of processing involving extraction, separation, and purification of a biological molecule from a biological sample, the sample processing device (2) described above is used for the series of processing, and included are the processes of:

setting the reaction containers on the reaction container set part when necessary, and independently performing movement control of each reaction container by the reaction container movement mechanism in a manner such that the corresponding processing part comes immediately below the integral stem in accordance with the series of processing; and performing control of entrance and leaving of the magnetic chip or the cover fitted to the corresponding stem into and from the processing part when the processing part comes immediately below the integral stem mechanism.

(Auxiliary Embodiments)

In the sample processing method of the present invention described above, the following optional embodiments are included.

(1) The stem mechanism cyclically and vertically moves in conjunction with the movement control of the reaction container, and is set in a manner such as to provide a predetermined stop time when the stem mechanism is at an upper dead point and a lower dead point.

(2) The reaction container includes an attachment and detachment mechanism of engaging and separating the magnetic chip or the cover by moving the magnetic chip or the cover in a decentered manner with respect to the processing part via the reaction container when the magnetic chip or the cover is inserted in the processing part, the attachment and detachment mechanism is composed of an upper retainer plate and a lower part retainer part provided above an opening of the processing part oppositely thereto, and the retainer plates are provided with notch regions receiving the movement in the decentered manner in compliance with outer diameters of the magnetic chip and the cover, the notch regions are arranged in a moving direction of the reaction container, and an opening of the each notch region is also directed in the moving direction of the reaction container, and the process of independently performing movement control of the reaction container by the reaction container movement mechanism includes control of, in addition to the movement between the processing parts, the movement of the magnetic chip and the cover in the decentered manner for the purpose of attaching and detaching the magnetic chip or the cover to and from the corresponding processing part.

(Reaction Container)

Further, as a reaction container using the sample processing device and method described above, the following are suggested.

Specifically, in a reaction container being used for extracting a biological molecule from a biological sample by using a reagent and a magnetic bead, being formed into a box shape, and being provided with a plurality of wells arranged in a box-shaped main body in a manner such that the series of processing are performed, provided as the wells are at least:

a reaction well to which the biological sample, the reagent for the biological molecule extraction, and the magnetic bead for biological molecule absorption are supplied;

a magnetic chip housing well housing a magnetic chip used for collecting the magnetic bead absorbing the biological molecule, for the purpose of attaching and detaching the magnetic chip to and from the stem; and a cover housing well housing a cover of the magnetic chip for the purpose of attaching and detaching the cover to and from the stem, further provided in the box-shaped main body is an attachment and detachment mechanism of engaging and separating the magnetic chip or the cover by moving the magnetic chip or the cover in a decentered manner with respect to the well via the reaction container when the magnetic chip or the cover is selectively in any one of the wells, the attachment and detachment mechanism is composed of an upper retainer plate and a lower part retainer part provided above an opening of the processing part oppositely thereto, and the retainer plates are provided with notch regions receiving the movement in the decentered manner in compliance with outer diameters of the magnetic chip and the cover, and the notch regions are provided in agreement with an arrangement direction of the wells, and openings of the notch regions are also directed in the well arrangement direction.

(Auxiliary Embodiments)

Moreover, in the reaction container according to the invention, the following optical embodiments are included.

(1) The upper retainer plate and the lower retainer plate are commonly used for the magnetic chip and the cover, and each retainer plate is compositely formed with notch elements having a curvature corresponding to the outer diameter of the magnetic chip and a curvature corresponding to the outer diameter of the cover.

(2) The upper retainer plate and the lower part retainer part are arranged separately for the magnetic chip and the cover, the upper retainer plate and the lower retainer plate for the magnetic chip are formed with notch regions with the curvature corresponding to the outer diameter of the magnetic chip, and the upper retainer plate and the lower retainer plate for the cover are formed with notch regions with the curvature corresponding to the outer diameter of the cover.

Advantageous Effects of Invention

The present invention can provide a sample processing device and a sample processing method capable of, in a series of processing (for example, processing involving extraction, separation, and purification of biological molecules such as nucleic acids and proteins) performed by causing reaction of biological samples with a regent, performing batch processing on the biological samples (specimens) and also performing successive processing through random introduction, and the invention can also provide a reaction container using these sample processing device and sample processing method.

DESCRIPTION OF EMBODIMENTS

Hereinafter, an embodiment of the present invention, especially a sample processing device and a sample processing method, and a reaction container using them will be described with reference to the drawings. Note that, however, the invention is not limited to the embodiment described here.

(Configuration of Sample Processing Device)

Figure 1:
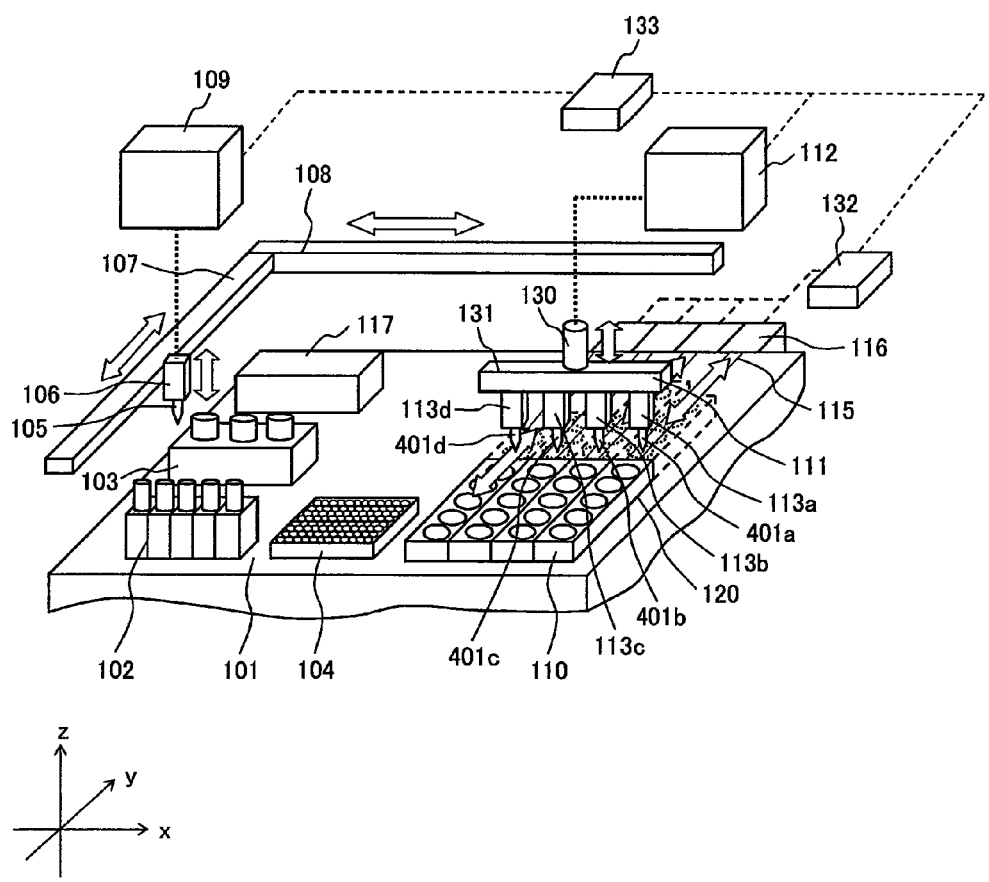
FIG. 1 is a perspective view schematically showing a configuration example of a sample processing device according to the present invention.

FIG. 1 schematically shows a configuration example of the sample processing device according to the invention. The sample processing device includes: a mounting base 101; a specimen rack 102 capable of storing sample containers filled with biological samples targeted for processing; a reagent rack 103 capable of storing a plurality of reagent bottles; a chip rack 104 storing a plurality of disposable tips; a waste container 117 for disposing wastes; a nozzle mechanism 105 arranged at position opposing one surface of the mounting base 101 in a manner such as to be movable in x-axis, y-axis, and z-axis directions; a driving control part 109 controlling movement, suction, and discharge of the nozzle mechanism 105; reaction containers 110 in which a series of processing of extracting, separating, and purifying biological molecules from biological samples is performed; an integral stem mechanism 111 used for performing the series of processing in cooperation with the reaction containers 110; a reaction container set part 120 on which a plurality of reaction containers 110 can be arranged in parallel; and a reaction container movement mechanism (reaction container loading stage 201, needles 202, a screw rod 203, and a servomotor (actuator) 116 in FIG. 2A) allowing each of the reaction containers to independently make a translational motion (straightforward motion).

The biological samples in this description are not specifically limited, but are: for example, (1) living body samples, such as blood, blood plasma, or tissue slice samples, body fluid, or urine that are obtained from creatures including a human being; (2) cells such as animal cells, vegetable cells, or insect cells, (3) microorganisms such as bacteria, fungus, or algae, and (4) viruses (including a virus transmitting cell). The biological samples contain a culture solution culturing these cells, microorganisms, and viruses and a suspending solution suspending these cells, microorganisms, and viruses. In addition, these biological samples contain biological molecules targeted for extraction, separation, and purification performed by the sample processing device. The biological molecules here mean nucleic acids such as DNA and RNA, proteins such as enzymes and antibodies, and peptide fragments. Targets of the extraction, separation, and purification performed by the sample processing device according to the invention are not limited to the nucleic acids, the proteins, and the peptide fragments, but also include compounds (organic compounds and low-molecule compounds) produced by the cells and the microorganisms.

The specimen rack 102 is formed into a box shape that permits storage of a plurality of specimen tubes filled with different or same biological samples. In the specimen rack 102, the plurality of specimen tubes are arranged in a manner such that they can be dispensed by the nozzle mechanism 105 and also the specimen tube already subjected to the dispensing can be taken out of the device and the next specimen tube can be set. The reagent rack 103 is formed into a box shape that permits storage of a plurality of reagent bottles. In the reagent rack 103, different reagent bottles can be stored depending on processing performed on biological samples. For example, when processing of extracting nucleic acid components from the biological samples is performed, the reagent rack 103 can store: a reagent bottle of a solution containing a chaotropic agent, a reagent bottle of a wash solution, a reagent bottle of an eluting solution, a reagent bottle of oil dispensed into the reaction container 110, etc.

The reaction container 110 is formed of a box-shaped container in which wells serving as a plurality of processing parts to be described below are arranged in a row. There are various types of wells, but illustrated in this example are: a cover housing well 501, a magnetic chip housing well 502, a reaction well 503, a washing well (#1) 504, a washing well (#2) 505, and an eluting well 506 in FIG. 5A. For the reaction container 110, a plurality of reaction containers can be collectively set in the sample processing device for the purpose of batch processing, but any given number of reaction containers can also be set. Moreover, it can be additionally set as needed, allowing the reaction containers to randomly proceed a series of processing independently from each other. The set part 120 for these reaction containers 110 includes a mechanism that allows each reaction container 110 to make a translational operation (straightforward operation) independently. This translational operation mechanism and the reaction containers will be described in detail later on.

The nozzle mechanism 105, not shown, has its inside formed into a cylinder shape and connected to a suction and discharge driving device such as a pump.

The nozzle mechanism 105 moves in an x-axis direction along a nozzle mechanism movement guide X108, moves in a y-axis direction along a nozzle mechanism movement guide Y107, and moves in a z-axis direction along a nozzle mechanism movement guide Z106. A driving mechanism allowing these movements in the three axes (the x-axis, the y-axis, and the z-axis) directions is well known, and thus its detailed description will be omitted. By a combination of the movements in the x-axis direction, the y-axis direction, and the z-axis direction, the nozzle mechanism 105 can suction and discharge specimens and reagents by moving between the specimen rack 102, the reagent rack 103, and the reaction container set part 120 on the mounting base 101. For example, the nozzle mechanism 105 can suction the specimens from the specimen rack 102, move to the reaction well 503 in the reaction container 110, and discharge the specimens to this well. The nozzle mechanism 105 can also suction the reagents from the reagent rack 103, move to the reaction well 503 in the reaction container 110, and discharge the reagents to this well. The nozzle mechanism 105 can also suction a wash solution from the reagent rack 103, move to the washing well (#1) 504 and the washing well (#2) 505 of the reaction container 110, and discharge the wash solution to these wells. The nozzle mechanism 105 can also suction extraction liquid from the reagent rack 103, move to the eluting well 506 of the reaction container 110, and discharge the extraction liquid to this well.

The nozzle mechanism 105 can be fitted, at its tip, with the disposable tips loaded on the chip rack 104. A user of the sample processing device, when necessary, can replace the disposable tip, fitted to the nozzle mechanism 105, with the disposable tip on the chip rack 104. The replacement of the disposable tip can avoid contamination and carry-over between the reagents or the samples. The disposable tip can be fabricated with resin, such as polyethylene, polypropylene, or polycarbonate, used as a material.

It is also possible for the user and a vendor of the sample processing device to previously put required reagents and wash solution in the plurality of wells in the reaction container. In this case, part or all of the reagent rack 103 is no longer required. Further, in downstream analysis, upon judgment that there is no effect of the carry-over and the contamination, part or all of the chip rack 104 may be made unnecessary.

Above the reaction container set part 120, an integral stem mechanism 111 is arranged in a manner such as to be movable vertically (in the z-axis direction). The integral stem mechanism 111 is composed of: a plurality of stems (401a to 401d); and a stem vertical movement mechanism 130 that integrally supports these stems and moves them in the z-axis direction. The plurality of stems (401a to 401d) are supported by a common support member 131 with respective stem holders (113a to 113d) in between, and makes a one-axis motion (in the z-axis direction) by the stem vertical movement mechanism 130 via this support member 131. As the stem vertical movement mechanism 130, there are various possible mechanisms including: a mechanism of converting a rotational motion of for example, a motor (actuator) into a straightforward motion, and a mechanism of performing a straightforward motion in the z-axis direction by turning on and off a solenoid (actuator), and it is not limited thereto as long as control can be performed by an electrical signal of an integral stem mechanism driving control part 112.

In this example, the stem vertical movement mechanism 130 vertically moves the support member 131 common to the plurality of stems, thereby collectively enabling vertical movement of the plurality of stems with one driving device. This can reduce the number of driving devices. However, it is not limited thereto. As a motor used as the servomotor (actuator) of the stem vertical movement mechanism 130, there is one for all the stems, and a rotation axis rotated thereby is common, but it is also possible to provide configuration such that a mechanism (for example, cam mechanism) of converting the rotation of the rotation axis in the z-axis direction is included in the individual stem and the stems vertically move by their respective cam actions. Moreover, it is also possible to include a mechanism like the solenoid in each of the stems and individually and vertically move the stems, if no cost problem arises.

These stems (401a to 402d) forms a row in a direction (the x-axis direction) crossing a moving direction (the y-axis direction) of the reaction container 110, and are arranged with pitches in accordance with pitches between the wells (processing parts) of the two reaction containers 110 arranged in parallel on the reaction container set part 120. Positions of the integral stem mechanism 111 (positions in the x-axis and y-axis directions) other than its position in the z-axis direction are fixed and, for example, are located above the given well at an initial position (position of a solid line of FIG. 1) of the reaction container 110 on the reaction container set part 120.

The integral stem mechanism 111 makes a cyclic vertical motion at timing defined by an integral stem mechanism driving control part 112.

The integral stem mechanism 111 includes a number of stems equal to a largest number of reaction containers 110 that can be set on the reaction container set part 120. In other words, on the reaction container set part 120, a number of reaction containers 110 equal to or smaller than the number of stems can be arbitrarily disposed. More specifically, for example, up to 8 to 12 series of stems of the integral stem mechanism 111 can be parallelized. The stem parallelization makes it possible to improve processing capability (through put) per unit time.

The reaction container 110 can move in the y-axis direction along a guide groove 115 at timing defined by a servomotor (actuator) 116 as described below (the reaction container 110 moves in a region of a solid line and a broken line in FIG. 1).

Moreover, the sample processing device includes a computer 133 that performs overall control of a nozzle mechanism driving control part 109, the integral stem mechanism driving control part 112, and a reaction container driving control part 132. To the computer 133, information related to processing conditions and biological test samples and various other pieces of information are inputted to generate a control signal for executing a sample processing method to be described below.

(Movement of Reaction Container)

Figure 2A:
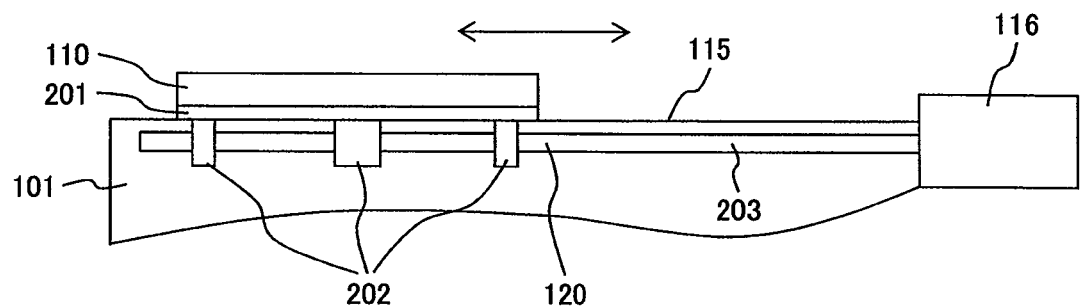
FIG. 2A is a cross section of a reaction container set part in FIG. 1, viewed from an x-axis direction.
Figure 2B:
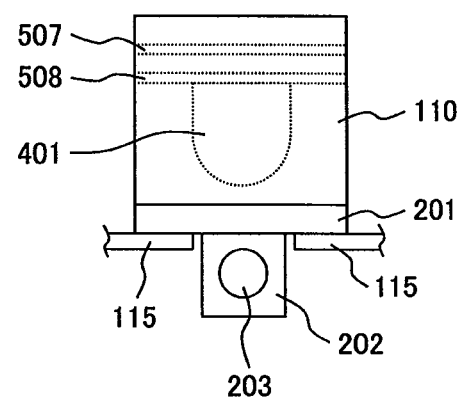
FIG. 2B is a cross section of the reaction container set part in FIG. 1, partially viewed from a y-axis direction.

FIG. 2A is a cross section of the reaction container set part 120 in FIG. 1, viewed from the x-axis direction, and FIG. 2B is a cross section of the reaction container in FIG. 1, viewed from the y-axis direction.

The reaction container 110 is mounted on a top surface of a stage 201. On a bottom surface of the stage 201, a plurality of needles 202 are attached. The needle 202 is provided with a female screw, through which a screw rod 203 penetrates. The screw rod 203 is driven into rotation by a servomotor (actuator) 116. The servomotors (actuators) 116 are included, the number of which is equal to the largest number of reaction containers 110 that can be set (parallelly arranged) on the reaction container set part 120, and their driving are controlled by a control signal from the reaction container driving control part 132. The driving of the servomotor (actuator) 116 permits the reaction container 110 to move in the y-axis direction (a direction of an arrow of FIG. 2A) along the guide groove 115 together with the stage 201.

The reaction containers 110 can be set on the reaction container set part 120 within a range in which the largest number of them can be set, and their (translational) movements are controlled in a well arrangement direction independently by their corresponding servomotors (actuators) 116. As shown in FIG. 1, in a case where a plurality of reaction containers (110a to 110d in FIG. 3A) are set (arranged in parallel) from the beginning, the individual reaction containers are controlled by their respective corresponding servomotors (actuators) 116. In this case, (i) in a case where processing executed on biological samples in the reaction containers 110a to 110d is the same, simultaneous control of movements of the servomotors (actuators) 116 respectively corresponding to the reaction containers results in interlocking control of this movement control and the integral stem mechanism 111 (one example of details of the interlocking control will be described in detail later on), whereby a series of processing is performed collectively on the set plurality of reaction containers (see FIG. 1). In addition, (ii) even in a case where an arbitrary number of the plurality of reaction containers are set in parallel from the beginning, it may be desired in some cases that biological samples of the respective reaction containers be different from each other, and/or their processing procedures be different from each other. In these cases, it is also possible to independently control movements of the reaction containers via the respective servomotors (actuators) 116 and perform control in accordance with respective processing conditions so that different well positions of the reaction containers come immediately below the integral stem mechanism 111. Further, (iii) in either of a case where the processing conditions are the same and a case where they are different, it is also possible to additionally set an arbitrary number of reaction containers on the reaction container set part as needed (that is, with time difference). Also in this case, as is the case with (ii), movements of the reaction containers are independently controlled via the respective servomotors (actuators) 116.

Figure 3A:
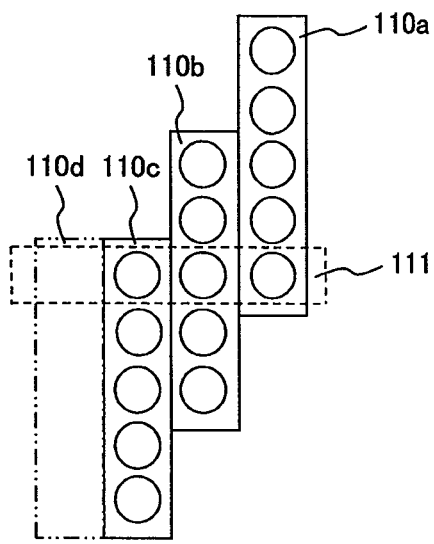
FIG. 3A is a plan view of a reaction container group showing one example of arrangement when reaction containers are set on the reaction container set part as needed and are moved independently from each other.

FIG. 3A shows a schematic plan view as one example of a case where movements of the reaction containers are controlled independently as in the (ii) and (iii) above. It is possible to perform sample processing successively as needed. That is, it is possible to perform successive processing by adding the next reaction container as needed without waiting for ending of processing performed on one reaction container.

FIG. 3A shows movement states of the reaction containers 110a to 110c after they were set with time difference as needed, and also shows an empty state that permits addition of the reaction container (110d) when necessary. For example, up to approximately 12 series of stems of the integral stem mechanism and reaction containers can be in parallel.

Figure 3B:
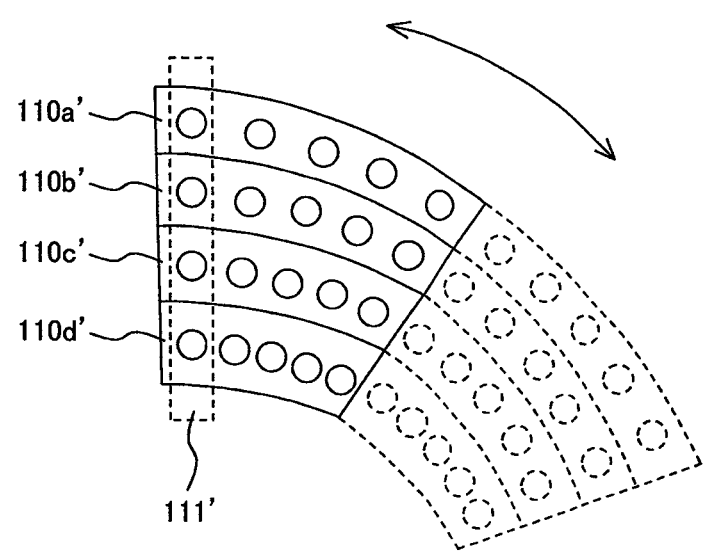
FIG. 3B is a plan view of a reaction container group showing another example of the arrangement when the reaction containers are set on the reaction container set part as needed and are moved independently from each other.

FIG. 3B shows a plan view of another embodiment example of reaction containers, a reaction container set part, and a reaction container movement mechanism. Illustrated in FIG. 3A are the reaction containers capable of making a translational motion independently from each other, but illustrated in FIG. 3B are, instead of them, reaction containers 110' (110a' to 110d') set in a manner such as to be movable in a rotation direction (directions of an arrow in the figure) with one axis (not shown) as a center independently from each other (the reaction containers 110a' to 110d' move in a region of a solid line and a broken line). A stem mechanism 111' performs the same operation as that of the already-mentioned stem mechanism 111 by a stem vertical movement mechanism. To move the reaction containers in the rotation direction, since moving distance per unit rotation angle becomes larger for the inner reaction container than for the outer reaction container, in correspondence therewith a pitch between the wells of each reaction container needs to be set. That is, for the reaction containers, the inner reaction container has a smaller pitch between the wells. Through the settings described above, in this embodiment, a reaction container group is formed into a sector shape when viewed from the top.

(Stem)

A stem 401 has different outer diameter parts provided from a stem tip side towards a stem middle region for the purpose of attaching and detaching a magnetic chip 402 and a cover 405 through openings of the magnetic chip and the cover.

Figure 4A:
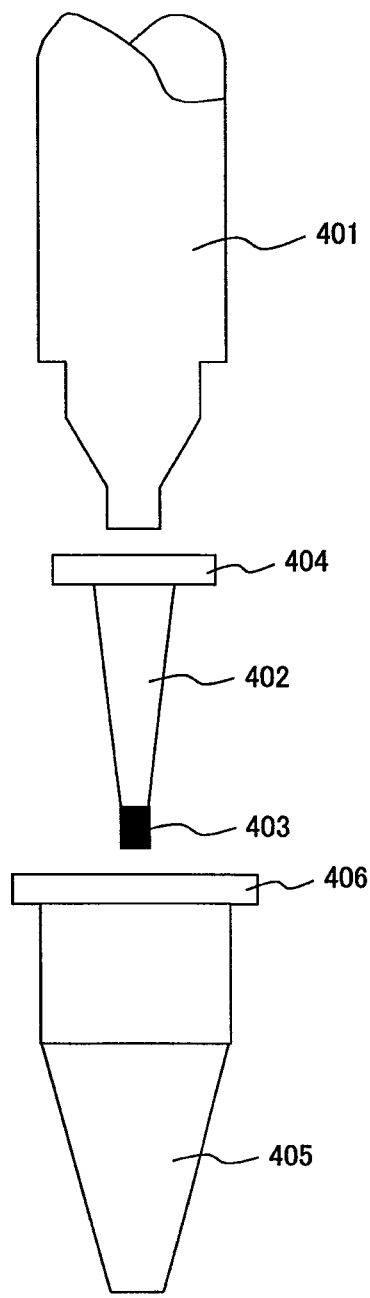
FIG. 4A is a diagram showing one example of a stem, a magnetic chip, and a cover of the sample processing device according to the present invention.
Figure 4B:
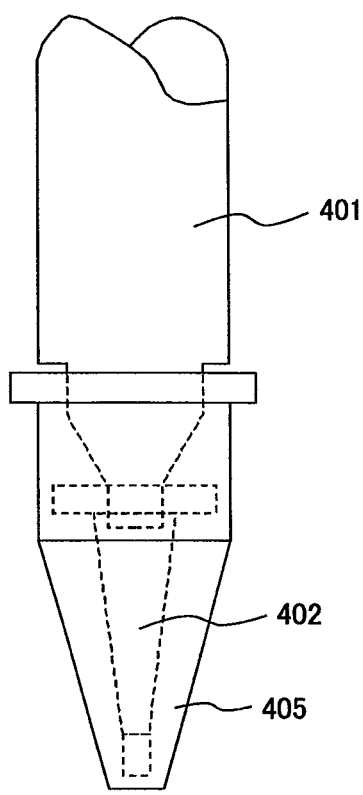
FIG. 4B is a diagram showing one example when the magnetic chip and the cover are fitted in the aforementioned stem.
Figure 4C:
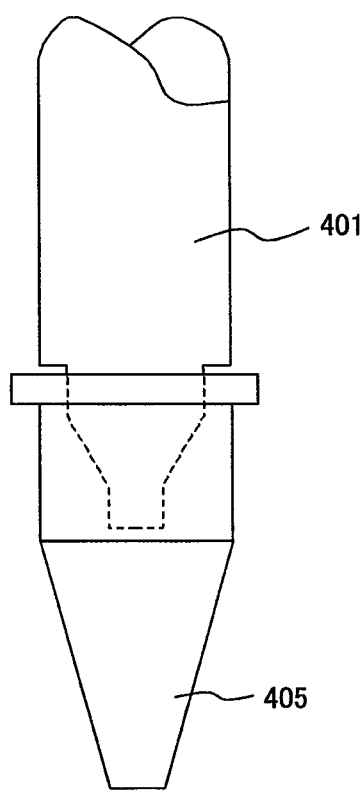
FIG. 4C is a diagram showing one example when the cover is fitted to the aforementioned stem.

FIGS. 4A to 4C each show one example of the stem 401, the magnetic chip (for example, a bar-like magnetic body) 402, and the cover 405 according to the invention. As shown in FIGS. 4A to 4C, it can be covered by both the magnetic chip 402 and the cover 405, or it can be covered directly by the cover 405 without being covered by the magnetic chip 402.

The magnetic chip 402 and the cover 405 each have an opening at its base end opposite to its tip, and an inner diameter of this opening region of the cover 405 is larger than that of the magnetic chip 402, and fringe regions (404 and 406) are provided at respective opening circumferential edges.

Moreover, the magnetic chip 402 has a base end region of which inner diameter is almost the same as that of a tip region of the stem 401, and is formed with this diameter decreasing towards the tip, so that the base end region of the magnetic chip 402 can be fitted into part of the stem 401 on the tip side. This magnetic chip 402 has, at its tip, a magnetic body 403 that generates a magnetic field.

The cover 405 has a base end region of which inner diameter is almost the same as that of a middle region of the stem 401, and is formed with its diameter decreasing towards the tip, so that the base end region of the cover 405 can be fitted into the middle region of the stem 401.

Used as a material for a portion of the magnetic chip 402 excluding the magnetic body and the cover 405 may be resin such as polyethylene, polypropylene, or polycarbonate.

(Reaction Container)

Figure 5A:
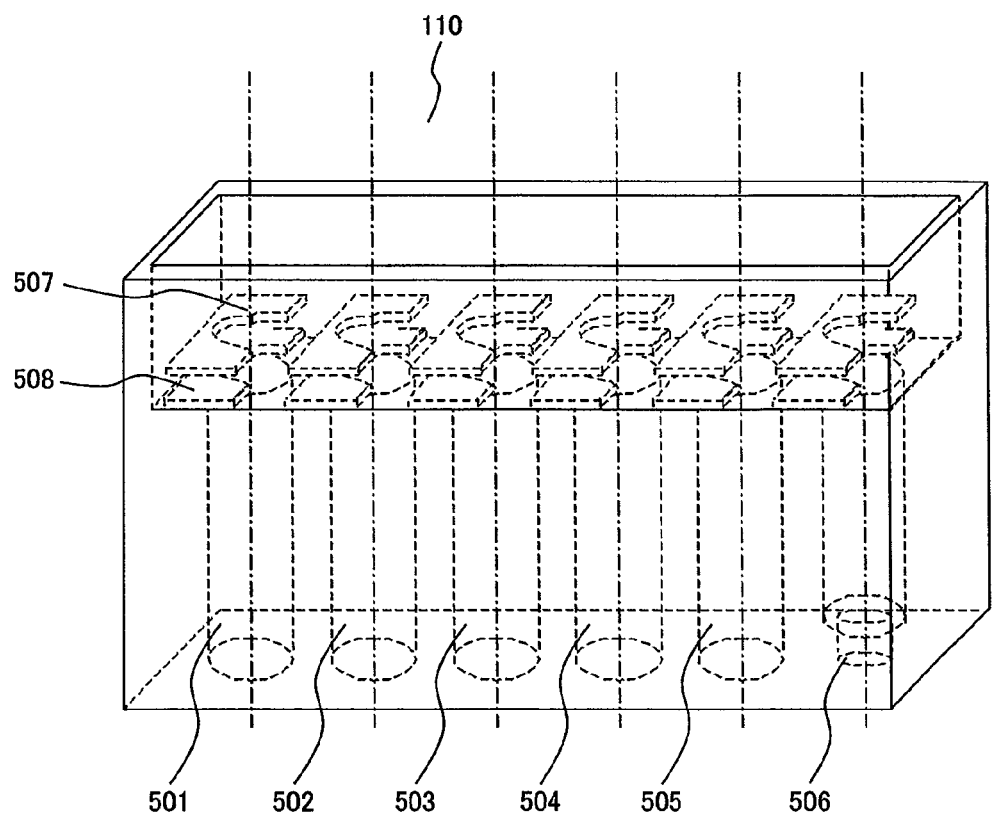
FIG. 5A is a perspective view showing a configuration example of the reaction container in the sample processing device according to the invention.

FIG. 5A shows a perspective view of a configuration example of the reaction container in the sample processing device according to the invention.

Figure 5B:
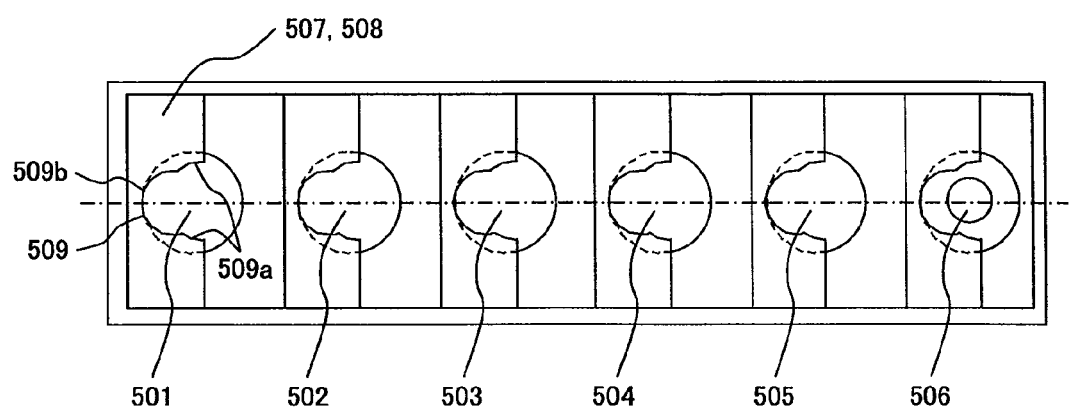
FIG. 5B is a plan view of the reaction container of FIG. 5A.

In addition, FIG. 5B shows a plan view of FIG. 5A.

The reaction container 110 is formed into a substantially box-like shape and has the wells 501 to 506 serving as the plurality of processing parts into which various reagents are dispensed.

Here, these wells are described as: the cover housing well 501, the magnetic chip housing well 502, the reaction well 503, the washing well (#1) 504, the washing well (#2) 505, and the eluting well 506, but kinds and the number of wells can be changed as appropriate in accordance with a kind of analysis. For example, in case of an analysis in which washing is important, a washing well may be added.

The plurality of wells 501 to 506 of the reaction container 110 are formed as depressed parts with predetermined volumes. Each well is formed with a depression of a depth that does not permit contact between a bottom surface of the well and the cover when the stem 401 fitted with the cover 405 arrives at a lower dead point. In this example, the eluting well 506 is formed as a depressed part shallower than the reaction wells 501 to 505 so that the eluting well 506 becomes smaller than the reaction wells 501 to 505 in volume.

The number of wells and their volumes are not specifically limited, and they can be set as appropriate in on biological samples.

Moreover, each well of the reaction container 110 is provided with an attachment and detachment mechanism for attaching and detaching the magnetic chip 402 and the cover 405 attached to the stem 401. Hereinafter, details of this attachment and detachment mechanism will be described.

The attachment and detachment mechanism is composed of: an upper retainer plate 507 and a lower retainer plate 508 for holding the magnetic chip 402 and the cover 405. The upper retainer plate 507 and the lower retainer plate 508 are arranged substantially in parallel to each other at a predetermined interval in between immediately above the opening of each well. Moreover, as shown in FIG. 5B, the upper retainer plate 507 and the lower retainer plate 508 are provided with a notch region 509 oppositely to each well, and the notch region 509 is of a potbelly type composed of notch elements 509a and 509b with two different kinds of curvatures. The notch element 509a has the curvature which is equal to or smaller than that of an outer diameter of the cover 405 and is larger than that of the fringe region 406 so as to achieve compliance with the outer diameter of the cover. The notch element 509b has the curvature which is equal to or smaller than that of an outer diameter of the magnetic chip 402 and is larger than that of the fringe region 404 so as to achieve compliance with the outer diameter of the magnetic chip.

As described above, with the notch elements 509a and 509b, the notch region 509 forms a two-stage notch structure. These notch elements, when viewed from the top, are formed such that the notch element 509b is located at a more rear position than the notch element 509a, the opening regions of the notch elements 509a and 509b are each directed to a center of the well, and one end opposite to the opening of the notch element 509b is located immediately or almost above an opening edge of the well. The respective notch regions 509 corresponding to the wells 501 to 506 are formed side by side on a straight line in a moving direction of the reaction container 110 when it is loaded on the reaction container set part 120. The openings of these notch elements 509a and 509b are directed to the aforementioned moving direction of the reaction container.

Figure 7A:
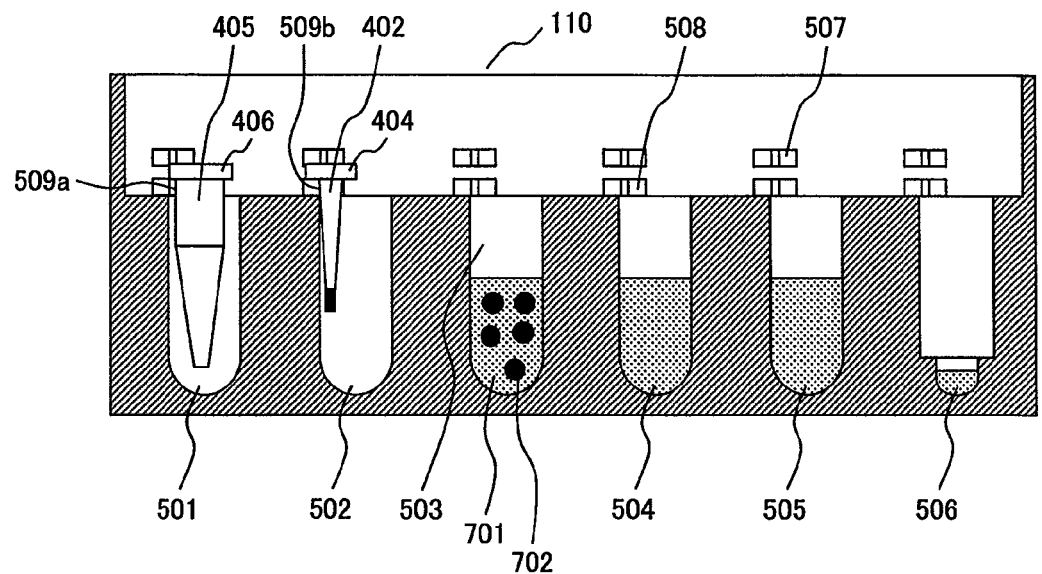
FIG. 7A is a sectional view showing the reaction container of the sample processing device according to this example.
Figure 7B:
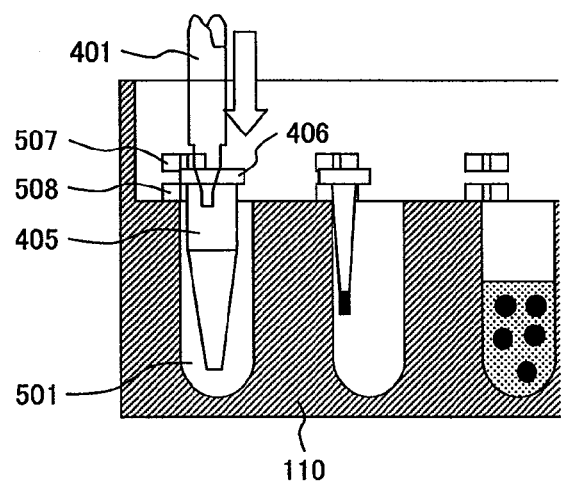
FIG. 7B is a schematic sectional view showing a stage at which the stem falls down to a cover housing well in a sample processing method according to an example of the invention.

As shown in FIGS. 7A and 7B, when the magnetic chip cover 405 is decentered towards the notch region 509 from the center of the well (501 to 506), part of an outer diameter of the magnetic chip cover 405 makes contact with the notch element 509a, so that part of the fringe region 406 is hooked by the upper and lower retainer plates 507 and 508. Moreover, when the magnetic chip 402 without any cover fitted thereto is further decentered towards the notch region 509 from the center of the well (501 to 506), part of an outer diameter of the magnetic chip 402 makes contact with the notch element 509b, so that part of the fringe region 404 are hooked by the upper and lower retainer plates 507 and 508. When the cover 405 and the magnetic chip 402 are located concentrically to the well or are at position decentered oppositely to the notch region 509, the fringe region 406 or the fringe region 404 is detached from the retainer plates 507 and 508, making it possible for the cover and the magnetic chip to be taken out of and into the well (be pulled from the well and inserted therein), that is, permitting attachment and detachment operation.

Figure 6A:
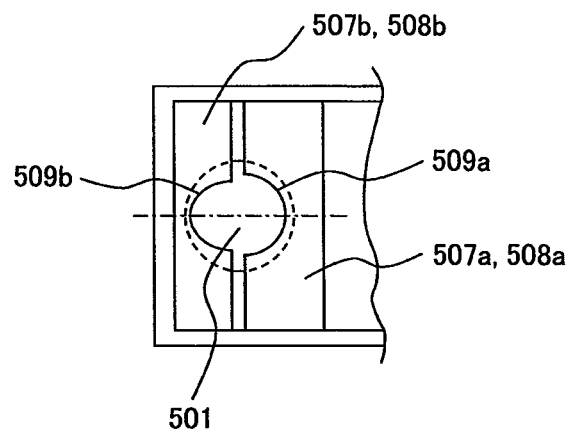
FIG. 6A is a plan view showing another configuration example of the reaction container in the sample processing device according to an example of the invention.
Figure 6B:
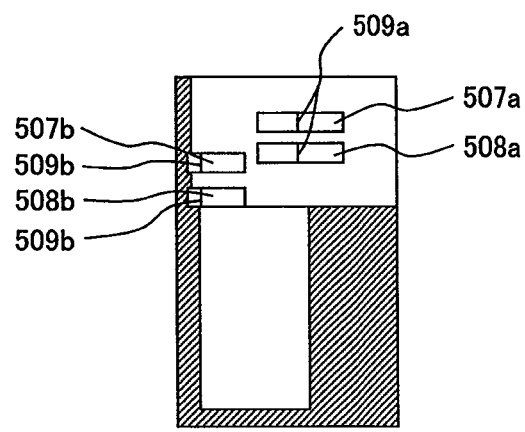
FIG. 6B is a sectional view of the reaction container of FIG. 6A.

In the example described above, a magnetic chip cover retainer plate and a magnetic chip retainer plate are formed by the common upper retainer plate 507 and lower retainer plate 508, and one notch region 509 is formed by the two-stage notch elements 509a and 509b formed at these retainer plates. Instead, as shown in FIGS. 6A and 6B, the magnetic chip cover retainer plate and the magnetic chip retainer plate may be provided separately from each other, and the former may be formed by an upper retainer plate 507a and a lower retainer plate 508a, and the latter may be formed by an upper retainer plate 507b and a lower retainer plate 508b, and further at the former and latter retainer plates, two kinds of notch elements (notch regions) 509a and 509b with different curvatures may be formed separately from each other. Moreover, the former and latter retainer plates may be arranged at different stages.

With such a notch structure, to hook the fringe region 406 of the cover 405 by the retainer plates 507a and 508a, the cover 405 may be decentered towards the notch element 509a with respect to the well. Moreover, to hook the fringe region 404 of the magnetic chip 402 by the retainer plates 507b and 508b, the magnetic chip 402 may be decentered towards the notch region 509b with respect to the well.

Openings of the notch regions 509a and 509b in this case are also directed towards the well center in the moving direction of the reaction container 110.

Moreover, at an upper part of each reaction well, an oil layer may also be added when necessary for the purpose of preventing volatilization and preventing liquid from being brought into the adjacent well. Such an oil layer technology is disclosed in Japanese Patent Application No. 2009-285343 as a former application of the applicant.

The magnetic chip 402 is previously housed in the magnetic chip housing well 502 (502 in FIG. 7A) and the whole reaction container 110 is set in the device. This housing may be carried out by a vendor that supplies the reaction containers, or may be carried out by the user each time.

The cover 405 is previously housed in the cover housing well 501 of the reaction container 110 (501 in FIG. 7A), and the whole reaction container 110 is set in the device. This housing may be carried out by the vendor that supplies the reaction containers, or may be carried out by the user each time.

The chip rack 104 has a plurality of opening regions storing a plurality of disposable tips. This opening region has a diameter that is a little larger than an outer diameter of the disposable tip and a little smaller than a fringe region of the disposable tip.

The waste container 117 is a container into which, for example, the used disposable tips, the magnetic chip 402, the cover 405, biological samples already subjected to processing, and a wash solution are disposed, and is formed into a box shape. Preferably, the waste container 117 includes a detachment mechanism, not shown, for detaching the disposable tip attached to part of the tip side or the middle region of the stem 401, the magnetic chip 402, and the cover 405. Adopted as the detachment mechanism can be, for example, a pushing plate that abuts the fringe region of the disposable tip, the fringe region 404 of the magnetic chip 402, and the fringe region 406 of the cover 405 and drives the stem 401 upward to thereby push the fringe regions downward. Note that the detachment mechanism may be provided in either one of the stem 401 and the waste container 117.

A nozzle mechanism driving control part 109, not shown, includes: a driving mechanism formed of, for example, a power source such as a motor, a gear mechanism that transmits power from the power source, and an arm; and a control substrate that outputs, to the driving mechanism, a control signal causing the aforementioned nozzle mechanism 105 to move along the x-axis, the y-axis, and the z-axis in FIG. 1 and perform dispensing operation through suction and discharge. To the control substrate, various conditions set by the operator on a computer 133 are inputted or various previously set conditions are read out for use.

The sample processing device described above had the configuration such that the reaction container 110 having the cover attachment and detachment mechanism is attached to the mounting base 101. However, the sample processing device may include a cover detachment mechanism at a position where the reaction container 110 is attached. That is, the sample processing device may have the cover detachment mechanism.

The sample processing device configured as described above can carry out various kinds of processing on biological samples.

Hereinafter, an example of a method of processing biological samples using the sample processing device with the configuration described above will be described.

EXAMPLE

Hereinafter, a sample processing method will be described, referring to, as an example, a mode in which processing of extracting a nucleic acid component from a biological sample is carried out.

More specifically, the sample processing method carries out the nucleic acid extraction by: (1) mixing the sample containing nucleic acids and other impure substances with silica-coated magnetic beads under the presence of a chaotropic agent; (2) absorbing the nucleic acids to surfaces of the magnetic beads, (3) separating the magnetic beads absorbing the nucleic acids, and (4) eluting the nucleic acids from the magnetic beads after washing. In addition, the integral stem mechanism 111 located above the plurality of reaction containers performs only simple vertical motion due to its integral type or preset cyclic vertical motion. The preset cyclic vertical motion refers to, for example, in a motion reciprocating between an upper dead point and a lower dead point, not a simple reciprocating motion, but a cyclic motion so set as to provide a stop time of 0.5 seconds at the upper dead point and the lower dead point, or at a particular height.

In this processing device, each of the reaction containers 110 independently makes a preset translational motion in the y-axis direction. For example, for the first reaction container 110a, if the stem 401 to which the cover 405 is attached needs to make a vertical motion in the washing well (#1) 504, the stage 201 on the mounting base 101 on which the reaction container 110a is mounted moves in the y-axis direction and stops when the washing well (#1) 504 is located immediately below the cover 405, the cover 405 directly connected to the integral stem mechanism 111 that makes a simple vertical motion consequently makes a vertical motion in the washing well (#1) 504. At this point, the adjacent reaction container 110b can be arranged at position completely different from that of the cover 405 by a program uniquely controlling its translational motion in the y-axis direction.

This translational motion in the y-axis direction that is independently made by each reaction container 110 makes it possible to load the reaction container 110 as needed if the reaction container 110 is not loaded on the stage 201, which can realize continuous sample loading.

As a more detailed motion of one reaction container stage, first, as shown in FIG. 7A, a biological sample targeted for processing and a solution 701 containing a chaotropic agent and a surface-active agent are dispensed into the reaction well 503, a wash solution is dispensed into the washing well (#1) 504 and the washing well (#2) 505, and an eluting solution is dispensed into the eluting well 506. Upon the dispensing of these solutions into the wells 501 to 506, the disposable tips are attached to the nozzle mechanism 105. To attach the disposable tips to the nozzle mechanism 105, the nozzle mechanism 105 is first moved through control performed by the nozzle mechanism driving control part 109 to a position where a center of a base end region of the disposable tip stored in the chip rack 104 and a tip region of the nozzle mechanism 105 accurately oppose each other (the nozzle mechanism. 105 moves in the x-axis and y-axis directions). Next, through control performed by the nozzle mechanism driving control part 109, the nozzle mechanism 105 is moved downward (in the z-axis direction), thereby making it possible to attach the disposable tip to the tip region of the nozzle mechanism 105. Through the aforementioned series of operations, the disposable tip can be attached to the nozzle mechanism 105.

Then in a state in which the disposable tip is attached, through control performed by the nozzle mechanism driving control part 109, the nozzle mechanism 105 is moved to above the reagent rack 103, a tip of the disposable tip is inserted into the reagent bottle, and a predetermined amount of solution is suctioned by a suction and discharge driving device such as pump means, not shown.

Then through control performed by the nozzle mechanism driving control part 109, the nozzle mechanism 105 is moved to above the reaction container 110, and the tip of the disposable tip is positioned above the predetermined well (any of 501 to 506). The suction and discharge driving device is activated in this state, so that the solution suctioned into the disposable tip can be dispensed into the predetermined well (any of 501 to 506)

Upon ending of the solution dispending, through control performed by the nozzle mechanism driving control part 109, the nozzle mechanism 105 is moved to above the waste container 117, and a detachment mechanism (not shown) attached to the nozzle mechanism 105 or the waste container 117 is activated to dispose the used disposable tip.

The aforementioned series of operations are common operations performed upon dispending of the wash solution, the eluting solution, or the solution containing the chaotropic agent and the surface-active agent. The dispending of the biological sample, excluding suction of a predetermined amount of biological sample from the specimen tube stored in the specimen rack 102, is carried out through the aforementioned series of operations. Moreover, illustrated is an example in which mutually different disposable tips are used upon the dispending of the wash solution, the eluting solution, the biological sample, and the solution containing the chaotropic agent and the surface-active agent, but the disposable tip may not be used depending on reaction. Moreover, the nozzle mechanism 105 carries out the dispensing of various types of reagents and a specimen on the device, but the dispensing of the various types of reagents to their reaction containers 110 may be previously carried out by their vendors, or may be previously carried out outside of the device by an analyzer. Moreover, the dispensing of the specimen can also be carried out outside of the device by the analyzer.

Next, as shown in FIG. 7A, to the reaction well 503 into which the biological sample targeted for processing have been dispensed, silica-coated magnetic beads 702 are dispensed by a magnetic bead dispensing mechanism, not shown. Note that the magnetic beads 702 may be previously dispensed into the reaction well 503 or a solution with the magnetic beads 702 dispersed therein may be dispensed into the reaction well 503 in the same manner as the aforementioned operation of the nozzle mechanism 105. Moreover, the biological sample is dispensed at a stage shown in FIG. 7A, but the biological sample may be dispensed together with the magnetic beads 702 or may be dispensed sequentially at this stage.

Here, the magnetic bead 702 may use any material, shape, and particle size as long as it has properties of a magnetic body conventionally used in, for example, a biotechnology field. Moreover, when nucleic acid extraction processing is to be carried out in the sample processing device, magnetic beads 702 having nucleic acid absorption capability are used. The nucleic acid absorption capability can be provided by coating a surface of the bead formed of a magnetic body with silica.

At this stage, the chaotropic agent is present in the reaction well 503, and thus a nucleic acid component contained in the biological sample is absorbed to the surface of the silica-coated magnetic bead 702.

Figure 7C:
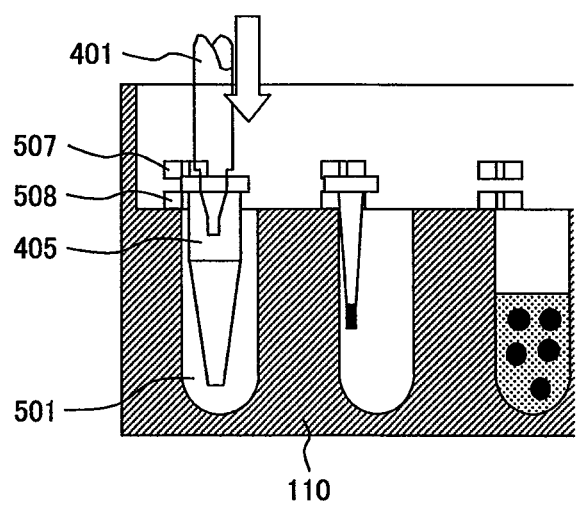
FIG. 7C is a schematic sectional view showing a process in which the cover is fitted to the stem in the sample processing method of this example.
Figure 7D:
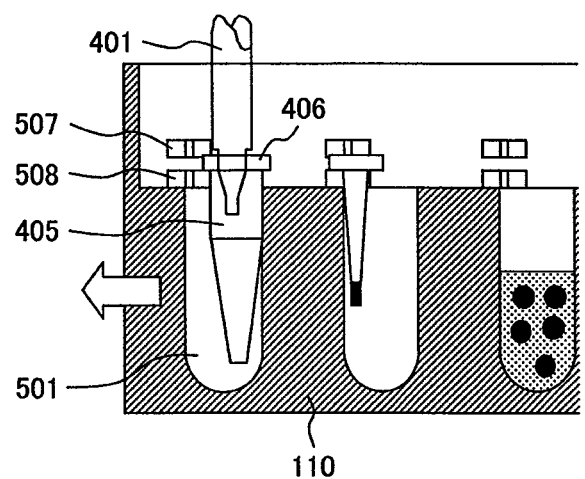
FIG. 7D is a schematic sectional view showing a process in which the reaction container moves (is decentered) in a y-axis direction after the cover is fitted in the sample processing method of this example.
Figure 7E:
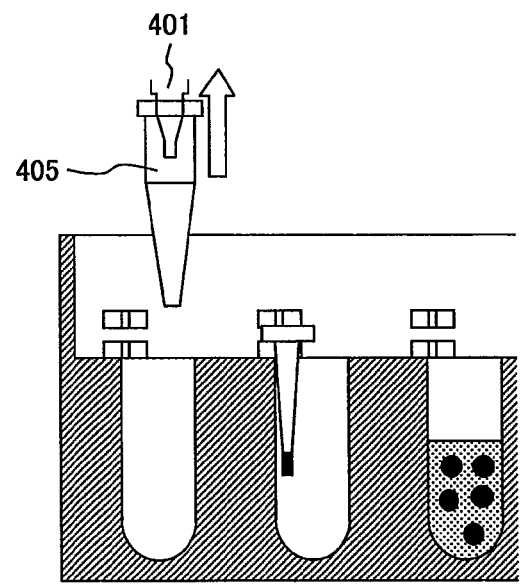
FIG. 7E is a schematic sectional view showing a rising process in which the steam fitted with the cover exits from the cover housing well in the sample processing method of this example.
Figure 7F:
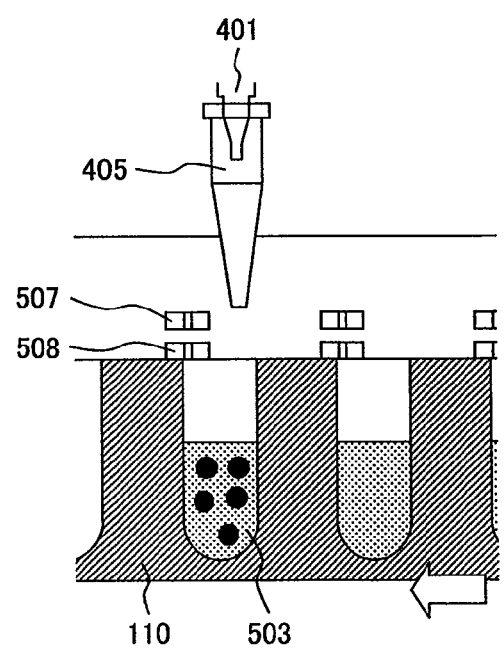
FIG. 7F is a schematic sectional view showing a process in which the reaction container moves in the y-axis direction so that a reaction well comes immediately below the stem fitted with the cover in the sample processing method of this example.

Moreover, at this stage, inside of the reaction well 503 may be stirred. To stir the inside of the reaction well 503, for example, permitted for use is a method of moving the magnetic beads 702 inside by cyclically applying a magnetic field from outside of the reaction container 110, or a method of attaching the cover 405 to the stem 401 and then controlling the integral stem mechanism 111 by the integral shaft mechanism driving control part 112 to oscillate the cover 405, attached to the stem 401, inside the reaction well 503 (FIG. 7H).

To an upper part of each reaction well, an oil layer may be added when necessary for the purpose of preventing volatilization and preventing liquid from being brought into the adjacent well.

The series of operations (nucleic acid extraction, separation, and purification) as a point of this example is performed as follows after preparing the cover 405, the magnetic chip 402, the reaction solutions (samples, reagents) and the magnetic beads, the wash solution, and the eluting solution in the wells 506 to 506, as shown in FIG. 7A. In the series of operations below, as described above, the integral stem mechanism ill is caused to makes vertical movement by the stem vertical movement mechanism, and each reaction container 110 is caused to move via the stage 201 in a well arrangement direction by each reaction container movement mechanism. Moreover, these movement mechanisms are controlled in an interlocking manner through the stem mechanism driving control part 112 and the reaction container driving control part 132 in accordance with control directions of the higher-class computer 113.

FIG. 7A shows a state in which the reaction container into which reagents containing magnetic beads and specimens have been dispensed is loaded on the reaction container set part 120 on the device.

The plurality of stems 401 make a cyclic vertical motion set at predetermined position (position shown in FIG. 1). Performed here is not simple reciprocating motion but cyclic motion set in a manner such as to provide a stop time of 0.5 seconds at the upper dead point and the lower dead point.

First, to stir compound liquid in the reaction well 503, the cover 405 is attached to the stem 401.

The reaction container 110 is moved so that the cover housing well 501 comes immediately below the stem 401 while the integral stem mechanism 111 is at the upper dead point and is also at a stop for 0.5 seconds (subsequent movements of the reaction container 110 are also made via the stage). After passage of a waiting time of 0.5 seconds, the stem 401 falls down (FIG. 7B), and the cover 405 is attached to the stem 401 (FIG. 7C). Cover attachment position is the lower dead point of the integral stem mechanism 111. To detach the cover from a cover holding part (gap between the upper retainer plate 507 and the lower retainer plate 508) of the reaction container, as shown in FIG. 7D, the reaction container 110 is slightly moved (decentered) in the y-axis direction (a direction of an arrow in FIG. 7D). Upon rising of the integral stem mechanism 111 at this point, as shown in FIG. 7E, the stem 401 and the cover 405 attached thereto are taken out from the reaction container 110.

The reaction container 110 is moved so that the reaction well 503 comes immediately below the stem 401 while the integral stem mechanism 111 is located above the reaction container 110 in FIG. 7F.

Figure 7G:
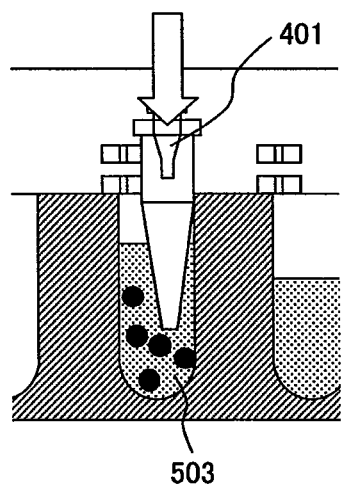
FIG. 7G is a schematic sectional view showing a process in which the stem fitted with the cover falls down to the reaction well in the sample processing method of this example.
Figure 7H:
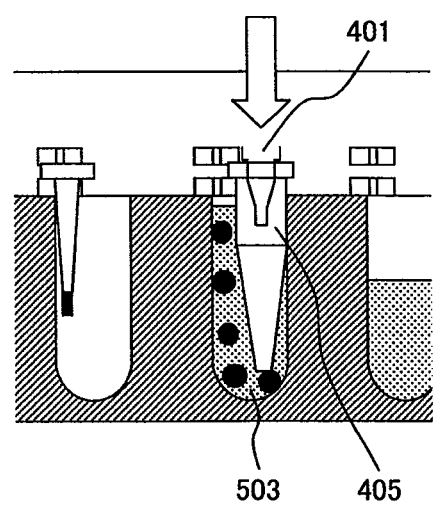
FIG. 7H is a schematic section view showing a process in which in the stem fitted with the cover falls down to the reaction well and arrives at a lower dead point in the sample processing method of this example.

In FIG. 7G, the integral stem mechanism ill falls down and enters into the reaction well 503. Position at which the stem 401 and the cover 405 fall down at this point is in a state decentered oppositely to the notch region 509 with respect to the well center. This makes it possible for the fringe region 406 of the cover 405 to fall down without interfering with the retainer plates 507 and 508.

Upon arrival of the integral stem mechanism 111 at the lower dead point in FIG. 7H, the stage 201 is under stop control at this position, and a plurality of times of stirring is performed by the cover 405.

After the stirring, the magnetic beads are washed as described below.

Figure 7I:
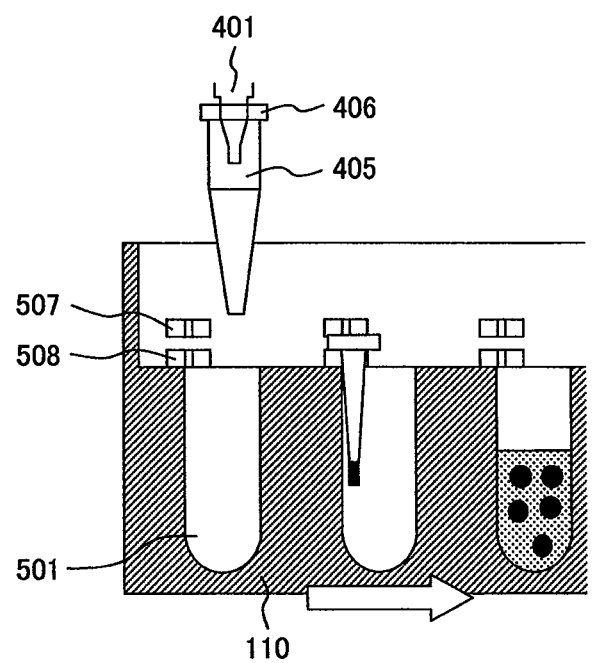
FIG. 7I is a schematic section view showing a process in which the reaction container moves in the y-axis direction so that the cover housing well comes immediately below the stem fitted with the cover in the sample processing method of this example.

The stage 201, when the integral stem mechanism 111 is at the upper dead point in FIG. 7I, moves the reaction container 110 so that the cover housing well 501 comes immediately below the cover 405.

Figure 7J:
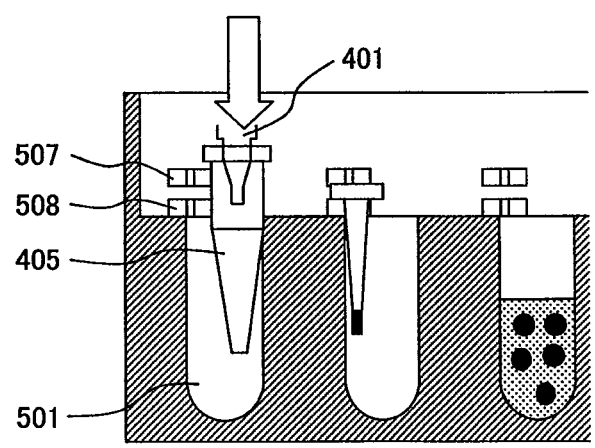
FIG. 7J is a schematic sectional view showing a process in which the stem fitted with the cover falls down to the cover housing well in the sample processing method of this example.
Figure 7K:
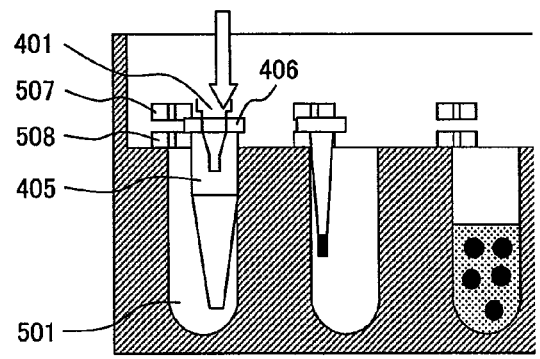
FIG. 7K is a schematic sectional view showing a process in which the stem fitted with the cover fall down to the cover housing well and arrives at a lower dead point in the sample processing method of this example.
Figure 7L:
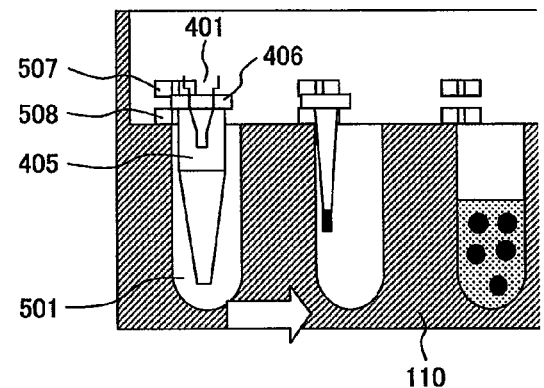
FIG. 7L is a schematic sectional view showing a process in which the stem fitted with the cover falls down to the cover housing well and arrives at the lower dead point, and then the reaction container moves (is decentered) in the y-axis direction in the sample processing method of this example.
Figure 7M:
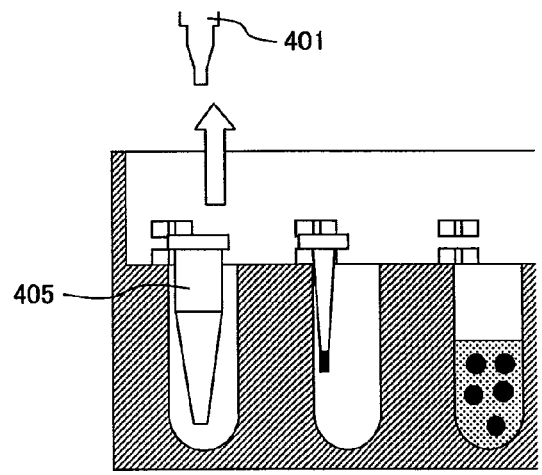
FIG. 7M is a schematic sectional view showing a process in which the stem separates from the cover and rises in the sample processing method of this example.

As a result of waiting at this position, the integral stem mechanism 111 falls down (FIG. 7J), arriving at the lower dead point (FIG. 7K). While the integral stem mechanism 111 is at a stop at the lower dead point for 0.5 seconds, the reaction container 110 is slightly moved (decentered) in the y-axis direction towards the notch region 509 (a direction of an arrow in FIG. 7L) so that the fringe region 406 of the cover 405 is sandwiched in the cover holding part (the gap between the upper retainer plate 507 and the lower retainer plate 508). As a result of waiting here, the integral stem mechanism 111 rises, so that the cover 405 is pressed by the retainer plates 507 and 508 and the cover 405 is detached from the stem 401 (FIG. 7M).

Figure 7N:
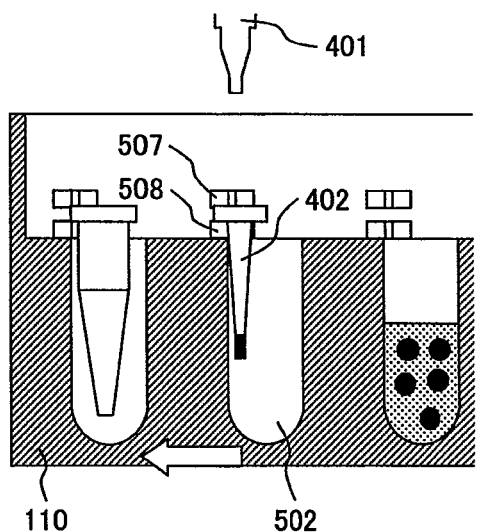
FIG. 7N is a schematic sectional view showing a process in which the reaction container moves in the y-axis direction so that a magnetic chip housing well comes immediately below the stem in the sample processing method of this example.
Figure 7O:
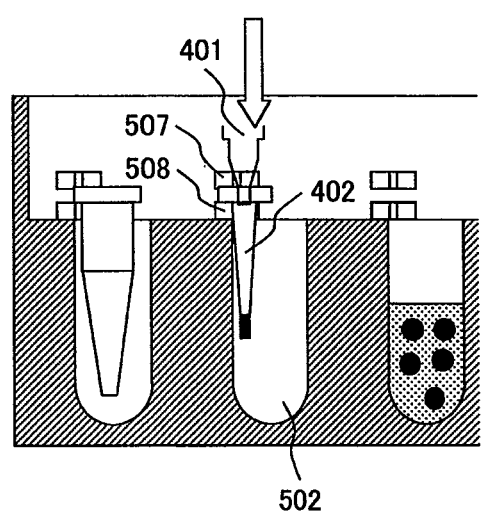
FIG. 7O is a schematic sectional view showing a process in which the stem falls down to the magnetic chip housing well in the sample processing method of this example.

Upon arrival of the integral stem mechanism 111 at the upper dead point in FIG. 7N, the reaction container 110 is moved so that the magnetic chip housing well 502 comes immediately below the stem 401. As a result of waiting here, as shown in FIG. 7O, the integral stem mechanism 111 falls down and the magnetic chip 402 is attached to the stem 401.

Figure 7P:
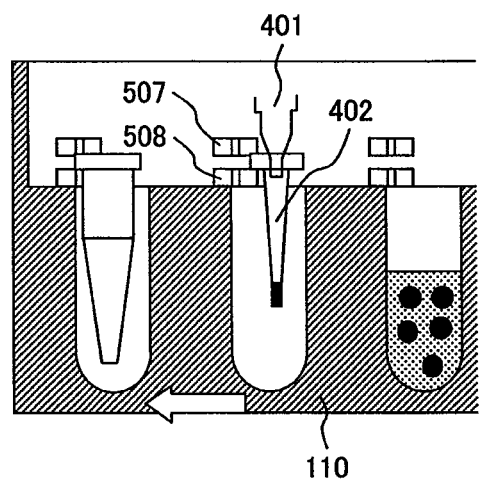
FIG. 7P is a schematic sectional view showing a process in which the reaction container moves in the y-axis direction in the sample processing method of this example.
Figure 7Q:
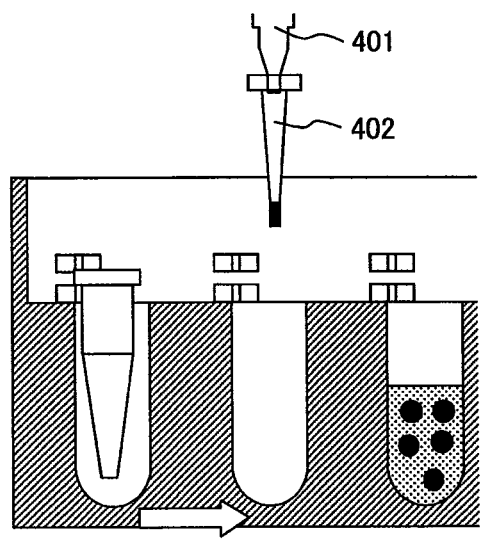
FIG. 7Q is a schematic sectional view showing a process in which the stem fitted with the magnetic ship rises in the sample processing method of this example.
Figure 7R:
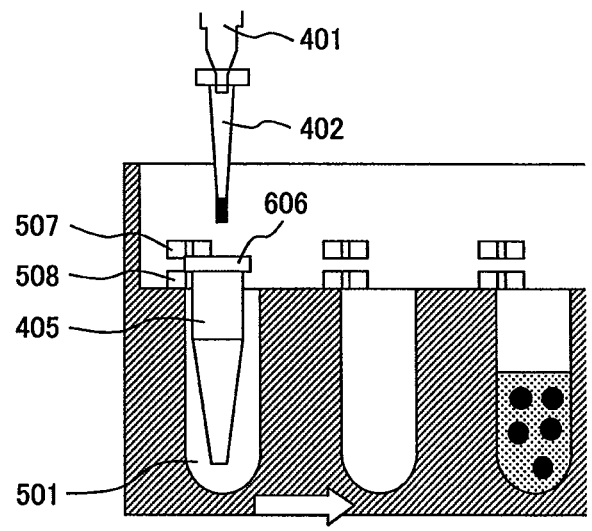
FIG. 7R is a schematic sectional view showing a process in which the reaction container moves in the y-axis direction so that the cover housing well comes immediately below the stem fitted with the magnetic chip in the sample processing method of this example.

The reaction container 110 is slightly moved in the y-axis direction (that is, decentered oppositely to the notch region 509) in FIG. 7P, the magnetic chip 402 is detached from the magnetic chip holding part (the gap between the upper retainer plate 507 and the lower retainer plate 508), and the integral stem mechanism ill is raised in FIG. 7Q, whereby the stem 401 fitted with the magnetic chip is located above the reaction container 110.

Figure 7S:
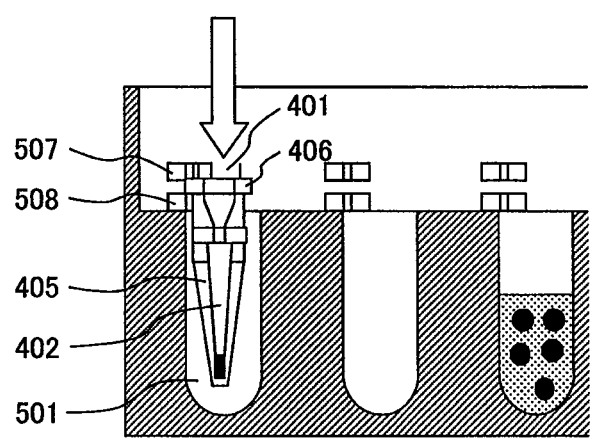
FIG. 7S is a schematic sectional view showing a process in which the stem fitted with the magnetic chip falls down to the cover housing well in the sample processing method of this example.
Figure 7T:
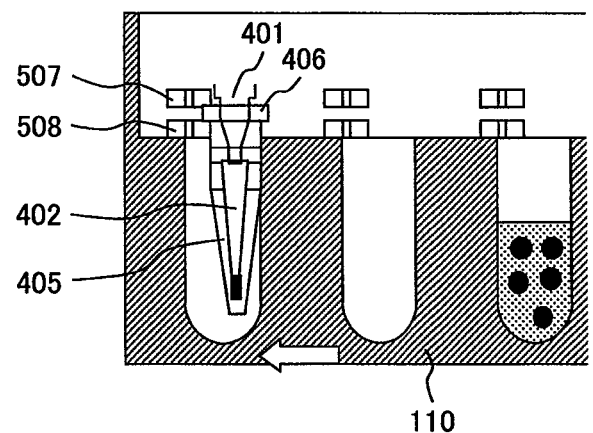
FIG. 7T is a schematic sectional view showing a process in which the reaction container moves (is decentered) in the y-axis direction after the stem fitted with the magnetic chip and the cover falls down to the cover housing well and arrives at the lower dead point in the sample processing method of this example.
Figure 7U:
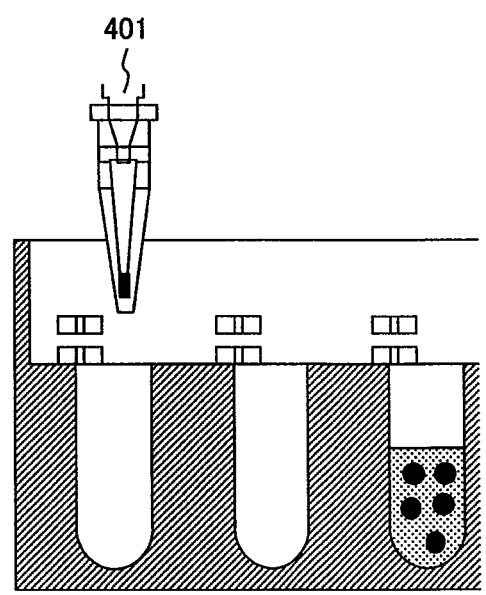
FIG. 7U is a schematic sectional view showing a process in which the stem fitted with the magnetic chip and the cover rises in the sample processing method of this example.

Through operations of FIGS. 7R to 7U, to the stem 401, the cover 405 is attached from the above the magnetic chip 402. Specifically, in FIG. 7R, the reaction container 110 is moved so that the cover housing well 501 comes immediately below the stem 401 fitted with the magnetic chip 402. In FIG. 7S, the integral stem mechanism 111 is dropped to make the stem 401 with the magnetic chip 402 enter into the cover housing well 501. As a result, the cover 405 is fitted to the stem 401. In FIG. 7T, the reaction container 110 is slightly moved in an arrow direction (moved in a direction in which the stem 401 with the cover and the magnetic chip is decentered oppositely to the notch region 509 with respect to the cover housing well 501). As a result, the stem 401 with the cover and the magnetic chip is detached from the retainer plates 507 and 508. In this state, as shown in FIG. 7U, the stem 401 with the cover and the magnetic chip is pulled up.

Figure 7V:
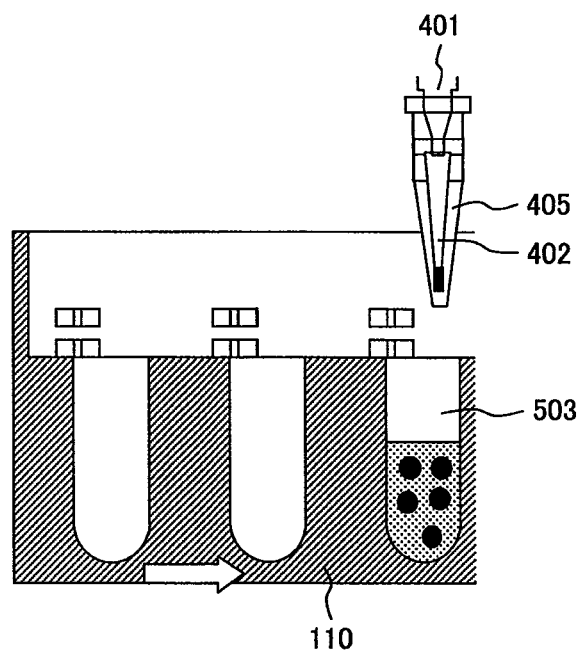
FIG. 7V is a schematic sectional view showing a process in which the reaction container moves in the y-axis direction so that the reaction well comes immediately below the stem fitted with the magnetic chip and the cover in the sample processing method of this example.
Figure 7W:
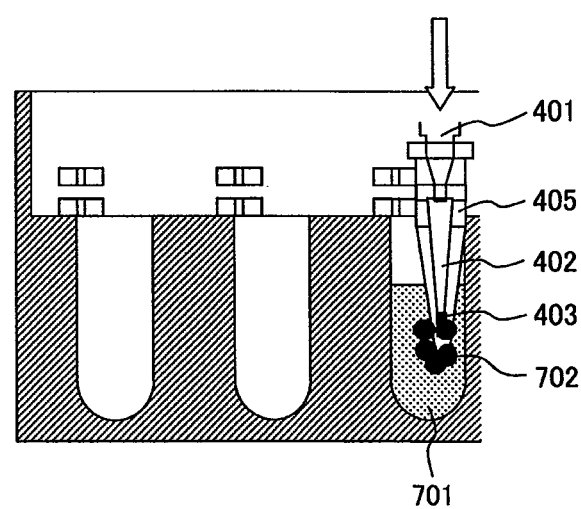
FIG. 7W is a schematic sectional view showing a process in which the stem fitted with the magnetic chip and the cover falls down to the reaction well in the sample processing method of this example.
Figure 7X:
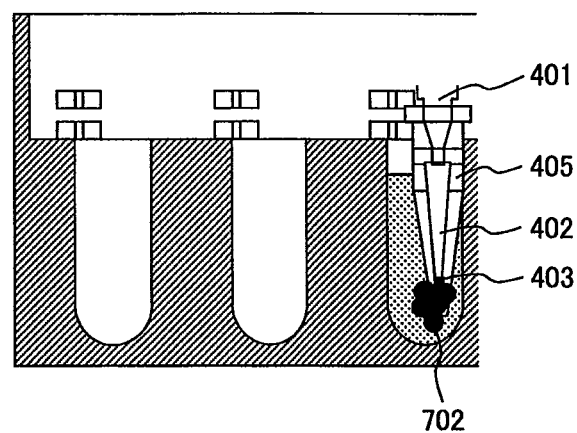
FIG. 7X is a schematic sectional view showing a process in which the stem fitted with the magnetic chip and the cover collects magnetic beads in the sample processing method of this example.
Figure 7Y:
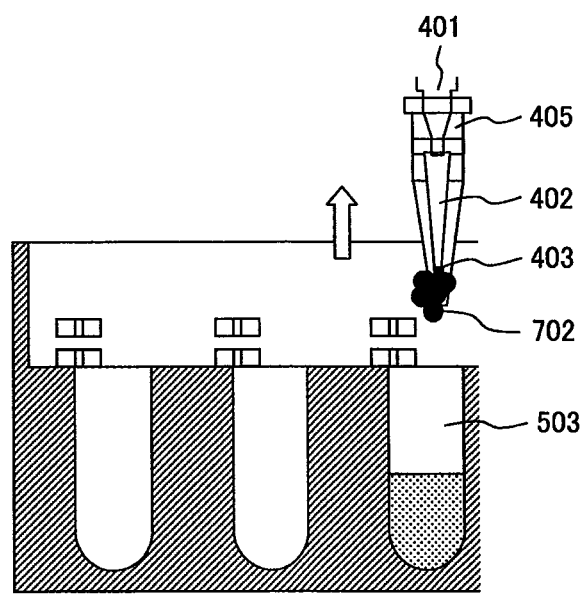
FIG. 7Y is a schematic sectional view showing a process in which the stem fitted with the magnetic chip and the cover rises while collecting the magnetic beads in the sample processing method of this example.

In FIG. 7V, the reaction container 110 is moved so that the reaction well 503 comes immediately below the stem 401 fitted with the magnetic chip 402 and the cover 405, and the reaction container 110 is stopped at this position. The integral stem mechanism 111 is dropped in FIG. 7W and the magnetic chip 402 and the cover 405 are made enter into the reaction well 503, upon which collection of the magnetic beads 702 is performed. In FIG. 7X, when the aforementioned magnetic bead collection is performed, the stem mechanism temporarily stops at the lower dead point, and then the integral stem mechanism 111 rises as shown in FIG. 7Y. In a case where the magnetic bead collection cannot be performed satisfactorily through one stem reciprocating (rising and falling) motion, the integral stem mechanism may be set in a manner such as to make reciprocation (rising and falling) a plurality of times.

Although not shown hereinafter, in a state in which the integral stem mechanism 111 is located above the reaction container 110 by the integral stem mechanism driving control part 112 (state in which the magnetic beads 702 are collected: state of 7Y), the reaction container 110 is moved so that the washing well (#1) 504 comes immediately below the magnetic chip 402 and the cover 405 (that is, immediately below the integral stem mechanism).

Then the integral stem mechanism 111 is dropped, causing the cover 405 and the magnetic chip 402 with the magnetic beads to enter into the washing well (#1) 504. After arrival of the integral stem mechanism 111 at the lower dead point, the reaction container 110 is slightly moved so that the fringe region 406 of the cover 405 is sandwiched (locked) between the retainer plates 507 and 508 above the washing well (#1) 504 (that is, the cover 405 is decentered towards the notch region 509 of the retainer plate). In this state, the cover 405 is remained, and in a state in which the magnetic chip 402 is fitted to the stem 401, the integral stem mechanism 111 is raised, and the reaction container 110 is moved so that the magnetic chip housing well 502 comes immediately below the integral stem mechanism 111. As a result of this operation, the magnetic beads 702 separate from the cover 405 and are immersed in the wash solution of the washing well (#1) 504. To return the magnetic chip 402 fitted to the stem 401 to the magnetic chip housing well 502, the integral stem mechanism 111 and the reaction container 110 are operated so as to perform reversed operations of FIGS. 7N to 7Q (that is, operations of FIGS. 7Q to 7N). Then the reaction container 110 is moved so that the washing well (#1) 504 comes again immediately below the integral stem mechanism 111. Then the integral stem mechanism 111 is dropped, the cover 405 locked between the retainer plates 507 and 508 of the washing well (#1) 504 is fitted to the stem 401 again, and the reaction container 110 is slightly moved and the integral stem mechanism 111 is caused to make a vertical motion so that the locking of the cover 405 against the retainer plates is released. As a result of this vertical motion, stirring is performed in the wash solution, and washing with the magnetic beads 702 is performed in the washing well (#1) 504. This washing makes it possible to remove impure substances such as proteins originating from the biological sample from the surfaces of the magnetic beads.

In the aforementioned washing, without performing the reversed operations of FIGS. 7N to 7Q, only raising the integral stem mechanism 111 (remaining the cover 405 between the retainer plates 507 and 508 in the washing well (#1) 504) separates the magnetic chip 402 together with the stem 401 from the cover 405, and thus the magnetic beads 702 are separated from the cover 405 and are immersed into the wash solution in the washing well. However, in this case, stirring effect brought by the vertical motion of the cover as described above cannot be expected, and washing time is longer than washing time of the one involving wash solution stirring.

After the first washing, the reaction container 110 and the integral stem mechanism 111 are subjected to movement control so that the magnetic chip 402 and the cover 405 are fitted to the stem 401 again, and this magnetic chip 402 and the cover 405 are located in the washing well (#1) 504, upon which the magnetic beads 702 are collected by the cover 405 again. The integral stem mechanism 111 is raised in a state in which the magnetic beads 702 are collected as described above, and the reaction container 110 is moved so that the washing well (#2) 505 comes immediately below the integral stem mechanism 111. Then, although not shown, the reaction container 110 and the integral stem mechanism 111 are operated in the same manner as the first washing, a second washing operation is carried out.

Next, the stem 401 fitted with the magnetic chip 402 and the cover 405 absorbing the already washed magnetic beads 702 is relatively moved to the eluting well 506 through vertical movement control of the integral stem mechanism 111 and control of movement of the reaction container 110 in the well arrangement direction. Then the same operations (control of stem vertical movement and control of movement of the reaction container in the arrangement direction) as the cover attachment and detachment operation and the magnetic chip attachment and detachment operation carried out in the washing process are also performed between the eluting well 506 and the magnetic chip housing well 502. As a result, the magnetic beads 702 are separated from the cover 405 and are immersed into the eluting solution in the eluting well 506. As already described above, each process can be realized only by the control of the cyclic vertical motion of the integral stem mechanism 111 by the stem mechanism driving control part 112 and the control of the translational motion of the reaction container 110 in the well arrangement direction (y-axis direction) by the reaction container driving control part 132.

In this eluting well 506, the nucleic acid components absorbed to the surfaces of the magnetic beads 702 can be eluted in the eluting solution. Through the above processes, the series of processing of nucleic acid extraction, separation, and purification are performed. Finally, the magnetic beads 702 in the eluting solution are collected at the tip of the cover 405 again by using the magnetic chip 402.

The already used magnetic chip 402 and cover 405 collecting the magnetic beads 702 are disposed, but in this example, by adding, to the integral stem mechanism 111, movement mechanisms (now shown) for the x-axis direction and the y-axis direction in addition to the movement mechanism 130 for the z-axis direction, moving the integral stem mechanism 111 to above the waste container 117 through control by the stem mechanism driving control part 112, and activating the detachment mechanism attached to the nozzle mechanism 105 or the waste container 117, the cover 405 and the magnetic chip 402 are disposed in the state in which the magnetic beads 702 are collected at their tips. Here, only the cover 405 may be detached and disposed while the magnetic chip 402 not in contact with the solution may be collected to be recycled.

The integral stem mechanism 111 may be provided with only the movement mechanism for the z-axis direction (stem vertical movement mechanism), and for the disposal of the magnetic chip 402 and the cover 405, the user can collect them by himself/herself and dispose them into a waste container at time of replacement of the reaction container 110. This only requires the integral stem mechanism to make the movement in the z-axis direction, which can therefore simplify the mechanism and the controls.

With the nucleic acid extraction method using the sample processing device according to this example, the magnetic beads 702 are collected at the tip of the cover 405 and moved to the reaction well 503 to the eluting well 506.

In conventional art, the same number of sample dispensing nozzles as that of reaction containers are prepared. In such conventional art, in a case where all specimens are processed in a batch, common reagents, and specimens at corresponding position can be suctioned and discharged with dispensing nozzles the number of which is equal to that of reaction containers by use of one syringe pump, but operation is the same in all the reaction containers, and thus it is typical batch processing. If each reaction container is structured to include a syringe pump, the syringe pump and xyz axes movement mechanisms need to be arranged in each reaction container, increasing device costs.

In this example, the dispensing inside the device is executed by one syringe pump, and a series of processing (stirring, magnetic bead collection, etc.) related to biological molecule extraction performed in the reaction container is realized by the movement of the integral stem mechanism in the z-axis motion and a single-axis motion of each reaction container in the y-axis direction. For the motion in the z-axis direction in particular, the number of axes is one without depending on the number of parallel processing, and to increase a degree of parallelism, one y-axis may be added to each reaction container, which can therefore reduce the device costs.

Further, with the sample processing device and the sample processing method of this example, in the series of processing involving the biological molecule extraction, separation, and purification by using the magnetic beads, a reaction container (specimen) can be randomly added to the device as needed, and the series of processing (for example, fracturing a cell and extracting biological molecules in the solution, separating the extracted biological molecules from the solution by the magnetic beads, and washing the magnetic beads and eluting (purifying) the biological molecules absorbed thereto by the eluting solution) can be carried out independently for each reaction container.

Further, for the reaction container of this example, an arrangement direction of the wells subjected to each processing matches the moving direction of the reaction container, and the magnetic chip and the notch regions of the attachment and detachment mechanism (retainer plates) for covering it, which are provided in the reaction container, are provided so as to match the well arrangement direction, and openings of these notch regions are also directed in the well arrangement direction, thus making it possible to provide a reaction container capable of carrying out the aforementioned sample processing method.

The invention claimed is:
1. A sample processing device including a plurality of reaction containers where a series of processing steps are performed by causing reaction of a biological sample with a reagent, each of the reaction containers being provided with a plurality of processing wells arranged in accordance with the series of processing steps performed, the sample processing device comprising:
 a reaction container set part having the plurality of the reaction containers arranged in parallel thereon;
 a reaction container movement mechanism configured to move each of the reaction containers set on the reaction container set part independently in an arrangement direction of the processing wells;
 a stem mechanism having a plurality of stems arranged in a row in a direction crossing a moving direction of the reaction containers above the reaction container set part, and arranged at a first pitch in accordance with a second pitch between the processing wells of the reaction containers arranged in parallel on the reaction container set part, the plurality of stems are used to perform the series of processing steps in cooperation with the movement of respective reaction containers by the reaction container movement mechanism;

a stem vertical movement mechanism configured to vertically move the stem mechanism; and a controller configured to interlock the reaction container movement mechanism and the stem vertical movement mechanism for the series of processing steps, and configured to control entry and exit of the corresponding stem or a tool fitted thereto into and out of the processing well when the corresponding processing well of each reaction container is immediately below the stem mechanism in accordance with a processing step of the series of processing steps.

2. The sample processing device according to claim 1, wherein a biological molecule is extracted from the biological sample in the processing well of the reaction container by use of a reagent for biological molecule extraction and a magnetic bead, the processing wells include, as the processing wells:

a reaction well containing at least the biological sample, the reagent for the biological molecule extraction, and the magnetic bead for biological molecule absorption;

a magnetic chip housing well housing a magnetic chip configured to engage and disengage with a stem of the plurality of stems, and collect the magnetic bead to which the biological molecule is absorbed, the magnetic chip housing well includes a magnetic chip housing part configured to engage with the magnetic chip and disengage with the magnetic chip;

a cover housing well housing a cover of the magnetic chip configured to engage and disengage with a stem of the plurality of stems, the cover housing well includes a cover housing well part configured to engage with the cover and disengage with the cover;

a washing well storing a wash solution that washes the magnetic bead to which the biological molecule is absorbed; and an eluting well configured to receive the washed magnetic bead and elute the biological molecule from a surface of the magnetic bead.

3. The sample processing device according to claim 1, wherein the stem mechanism is an integral stem mechanism in which the plurality of stems are supported integrally in a manner such as to be vertically movable;

the stem vertical movement mechanism has a mechanism configured to cause the integral stem mechanism to make a cyclic, vertical motion by one driving source through a control signal from the controller, and the reaction container movement mechanism is subjected to movement control by the controller in accordance with the cyclic, vertical motion of the stem vertical movement mechanism so that the plurality of processing wells align immediately below the stem vertical movement mechanism in accordance with the processing steps.

4. The sample processing device according to claim 1, wherein the reaction container movement mechanism is configured to linearly move each reaction container set on the reaction container set part.

5. The sample processing device according to claim 1, wherein the reaction container movement mechanism moves the reaction containers set on the reaction container set part in a rotation direction with one axis as a center.

6. The sample processing device according to claim 2, wherein the magnetic chip and the cover each have an opening at a base end thereof opposite to a tip end thereof, an inner diameter of the opening of the cover is larger than an inner diameter of the opening of the magnetic chip, and a fringe region is provided at a circumference edge of each opening, the stem includes parts having different outer diameters to allow the engagement and disengagement of the magnetic chip and the cover through the respective openings are provided from a stem tip side to a stem middle region, and the reaction container is provided with an attachment and detachment mechanism of engaging and separating the magnetic chip or the cover by moving the magnetic chip or the cover in a decentered manner via the reaction container with respect to the processing well when the magnetic chip or the cover is inserted into the processing well.

7. The sample processing device according to claim 6, wherein the attachment and detachment mechanism is comprised of an upper retainer plate and a lower retainer plate being provided above the opening of the processing well oppositely thereto, the retainer plates being provided with notch regions with different curvatures receiving the movement in the decentered manner in accordance with outer diameters of the magnetic chip and the cover, and the notch regions are arranged in a moving direction of the reaction containers and an opening of each of the notch regions is also directed in the moving direction of the reaction containers.

8. A sample processing device including a plurality of reaction containers where a series of processing steps related to at least extraction of a biological molecule from a biological sample by using a reagent and a magnetic bead is performed, the sample processing device comprising:

a plurality of reaction containers being provided with a plurality of processing wells arranged in accordance with the series of processing steps performed;

a reaction container set part having the plurality of the reaction containers arranged in parallel thereon;

a reaction container movement mechanism configured to move each of the reaction containers set on the reaction container set part independently in an arrangement direction of the processing wells;

a stem mechanism having a plurality of stems arranged in a row in a direction crossing a moving direction of the reaction containers above the reaction container set part, and arranged at a first pitch in accordance with a second pitch between the processing wells of the reaction containers arranged in parallel on the reaction container set part, the plurality of stems are used to perform the series of processing steps in cooperation with the movement of respective reaction containers by the reaction container movement mechanism;

a stem vertical movement mechanism configured to vertically move the stem mechanism; and a controller configured to interlock control of movement of each of the reaction containers in the processing well arrangement direction and the vertical movement of the stem vertical movement mechanism for the series of processing steps, and configured to control entry and exit of the corresponding stem or the magnetic chip and the cover fitted thereto into and out of the processing well when one of the processing wells is immediately below the stem mechanism in accordance with a step of the series of processing steps, wherein the biological molecule is extracted from the biological sample in the processing well of the reaction container by using the regent and the magnetic bead, the processing wells include, as the processing wells, at least:

a reaction well containing at least the biological sample, the reagent for the biological molecule extraction, and the magnetic bead for biological molecule absorption;

a magnetic chip housing well housing a magnetic chip configured to engage and disengage with a stem of the plurality of stems, and collect the magnetic bead to which the biological molecule is absorbed, the magnetic chip housing well includes a magnetic chip housing part configured to engage with the magnetic chip and disengage with the magnetic chip; and a cover housing well housing a cover of the magnetic chip configured to engage and disengage with a stem of the plurality of stems, the cover housing well includes a cover housing well part configured to engage with the cover and disengage with the cover.

9. The sample processing device according to claim 8, further comprising as the processing wells:

a washing well storing a wash solution that washes the magnetic bead to which the biological molecule is absorbed; and an eluting well configured to receive the washed magnetic bead and elute the biological molecule from a surface of the magnetic bead.

10. A sample processing method performing a series of processing including at least extraction, separation, and purification of a biological molecule from a biological sample, wherein the sample processing device according to claim 8, is used for the series of processing, the sample processing method comprising the processes of:

setting the reaction containers on the reaction container set part when necessary, and performing movement control of each of the reaction containers on the reaction container set part independently by the reaction container movement mechanism in a manner such that the corresponding processing well becomes aligned immediately below the stem mechanism in accordance with a processing step of the series of processing; and performing control of entry and exit of the magnetic chip or the cover fitted to the corresponding stem into and out of the processing well when the processing well is aligned immediately below the stem mechanism.

11. The sample processing method according to claim 10, wherein the stem mechanism cyclically and vertically moves in conjunction with the movement control of the reaction container, and the stem mechanism stops for a predetermined stop time when the stem mechanism is at an upper dead point and a lower dead point.

12. The sample processing method according to claim 10, wherein the reaction container includes an attachment and detachment mechanism of engaging and separating the magnetic chip or the cover by moving the magnetic chip or the cover in a decentered manner with respect to the processing well via the reaction container when the magnetic chip or the cover is inserted in the processing well, the attachment and detachment mechanism is composed of an upper retainer plate and a lower part retainer part provided above an opening of the processing well oppositely thereto, and the retainer plates are provided with notch regions receiving the movement in the decentered manner in compliance with outer diameters of the magnetic chip and the cover, the notch regions are arranged in a moving direction of the reaction container, and an opening of the each notch region is also directed in the moving direction of the reaction container, and the process of independently performing movement control of the reaction container by the reaction container movement mechanism includes control of, in addition to the movement between the processing well, the movement of the magnetic chip and the cover in the decentered manner for the purpose of attaching and detaching the magnetic chip or the cover to and from the corresponding processing well.

* * * * *